(12) United States Patent
Northrop et al.

(10) Patent No.: US 10,252,024 B2
(45) Date of Patent: Apr. 9, 2019

(54) MEDICAL DEVICES AND METHODS OF MANUFACTURING SAME

(71) Applicants: Stryker Corporation, Kalamazoo, MI (US); Stryker European Holdings I, LLC, Kalamazoo, MI (US)

(72) Inventors: Clay Northrop, Salt Lake City, UT (US); Ted Layman, Park City, UT (US); Stephen Porter, Piedmont, CA (US); James Paul, Salt Lake City, UT (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 215 days.

(21) Appl. No.: 15/091,443

(22) Filed: Apr. 5, 2016

(65) Prior Publication Data
US 2017/0281909 A1    Oct. 5, 2017

(51) Int. Cl.
*A61M 25/00*    (2006.01)
*A61M 25/09*    (2006.01)

(52) U.S. Cl.
CPC ............ *A61M 25/0013* (2013.01); *A61M 2025/09108* (2013.01); *A61M 2025/09133* (2013.01)

(58) Field of Classification Search
CPC ...... A61M 25/0013; A61M 25/09; A61B 5/00
USPC .......................................... 600/585; 427/2.1
See application file for complete search history.

(56) References Cited

U.S. PATENT DOCUMENTS

| | | | |
|---|---|---|---|
| 5,916,177 A | 6/1999 | Schwager | |
| 6,001,068 A | 12/1999 | Uchino et al. | |
| 6,004,279 A | 12/1999 | Crowley | |
| 6,017,319 A | 1/2000 | Jacobsen et al. | |
| 6,130,406 A | 10/2000 | Cheer | |
| 6,183,424 B1 | 2/2001 | Schwager | |
| 6,203,732 B1 | 3/2001 | Clubb et al. | |
| 6,428,489 B1* | 8/2002 | Jacobsen ........... A61M 25/0054 600/585 |
| 6,440,088 B1 | 8/2002 | Jacobsen et al. | |
| 6,500,130 B2 | 12/2002 | Kinsella et al. | |
| 6,579,246 B2 | 6/2003 | Jacobsen et al. | |
| 6,585,719 B2 | 7/2003 | Wang | |
| 6,652,508 B2 | 11/2003 | Griffin et al. | |
| 6,685,679 B2 | 2/2004 | Merdan | |
| 6,716,207 B2 | 4/2004 | Farnholtz | |

(Continued)

*Primary Examiner* — Andrew J Bowman
(74) *Attorney, Agent, or Firm* — Vista IP Law Group LLP

(57) ABSTRACT

A method of forming a fenestrated tubular support member includes determining a first iso-stiffness curve corresponding to a first function of beam length versus ring width for the first stiffness; determining a second iso-stiffness curve corresponding to a second function of beam length versus ring width for the second stiffness; determining an iso-volume curve corresponding to a third function of beam length versus ring width for a given fenestration volume; identifying a first intersection point where the iso-volume curve intersects the first iso-stiffness curve; and identifying a second intersection point where the iso-volume curve intersects the second iso-stiffness curve. The first section ring width and first section beam length are determined from the first intersection point, and the second section ring width and second section beam length are determined from the second intersection point.

14 Claims, 19 Drawing Sheets

(56) References Cited

U.S. PATENT DOCUMENTS

| | | |
|---|---|---|
| 6,719,748 B2 | 4/2004 | Wang |
| 6,786,876 B2 | 9/2004 | Cox |
| 7,258,753 B2 | 8/2007 | Abrams et al. |
| 7,494,687 B2 | 2/2009 | Cox |
| 7,682,337 B2 | 3/2010 | Valaie |
| 7,771,410 B2 | 8/2010 | Venturelli |
| 7,785,273 B2 | 8/2010 | Eskuri |
| 7,824,443 B2 | 11/2010 | Salahieh et al. |
| 7,828,832 B2 | 11/2010 | Belluche et al. |
| 7,857,008 B2 | 12/2010 | Chen |
| 7,878,984 B2 | 2/2011 | Jacobsen et al. |
| 7,955,272 B2 | 6/2011 | Rooney et al. |
| 7,989,042 B2 | 8/2011 | Obara et al. |
| 8,007,434 B2 | 8/2011 | Olson |
| 8,048,060 B2 | 11/2011 | Griffin et al. |
| 8,157,766 B2 | 4/2012 | Bonnette et al. |
| 8,172,829 B2 | 5/2012 | Farnholtz |
| 8,182,465 B2 | 5/2012 | Griffin et al. |
| 8,224,417 B2 | 7/2012 | Vetter |
| 8,292,827 B2 | 10/2012 | Musbach et al. |
| 8,460,213 B2 * | 6/2013 | Northrop ............ A61B 1/00071 600/585 |
| 8,468,919 B2 | 6/2013 | Christian et al. |
| 8,485,992 B2 | 7/2013 | Griffin et al. |
| 8,708,953 B2 | 4/2014 | Salahieh et al. |
| 8,715,315 B1 | 5/2014 | Janardhan et al. |
| 8,721,676 B1 | 5/2014 | Janardhan et al. |
| 8,795,320 B2 | 8/2014 | Strauss et al. |
| 8,805,468 B2 | 8/2014 | Vetter |
| 8,816,247 B1 | 8/2014 | Janardhan et al. |
| 8,864,789 B2 | 10/2014 | Balgobin et al. |
| 8,864,790 B2 | 10/2014 | Strauss et al. |
| 8,872,068 B1 | 10/2014 | Janardhan et al. |
| 8,895,891 B2 | 11/2014 | Janardhan et al. |
| 8,911,814 B2 | 12/2014 | Chen |
| 8,968,383 B1 | 3/2015 | Johnson et al. |
| 2003/0069522 A1 | 4/2003 | Jacobsen et al. |
| 2005/0124976 A1 | 6/2005 | Devens, Jr. et al. |
| 2009/0177119 A1 | 7/2009 | Heidner et al. |

* cited by examiner

| Fig. # | EI (in²-lb) | Beam Length (in.) | Slot Spacing (in.) | Slot Width (in.) |
|---|---|---|---|---|
| 5 | 1.51E-4 | 0.003 | 0.00557 | 0.00157 |
| 6 | 9.52E-4 | 0.0025 | 0.00557 | 0.00157 |
| 7 | 3.90E-4 | 0.005 | 0.00557 | 0.00157 |
| 8 | 3.44E-5 | 0.003 | 0.00327 | 0.00157 |
| 9 | 7.98E-5 | 0.003 | 0.00557 | 0.00157 |
| 10 | 1.79E-4 | 0.003 | 0.00557 | 0.00070 |
| 11 | 4.96E-4 | 0.0045 | 0.00757 | 0.00157 |
| 12 | 5.25E-4 | 0.0045 | 0.00757 | 0.00157 |
| 13 | $1^{st}$ = 1.60E-5 $2^{nd}$ = 8.68E-5 | $1^{st}$ = 1.05E-3 $2^{nd}$ = 4.81E-3 | $1^{st}$ = 4.73E-3 $2^{nd}$ = 3.54E-3 | 0.00157 |
| 14 | 2.3E-4 | $1^{st}$ (3 b) = 1.55E-3 $2^{nd}$ (2 b) = 3.67E-3 | $1^{st}$ (3 b) = 3.12E-3 $2^{nd}$ (2 b) = 5.24E-3 | 0.00157 |

FIG. 15

MEDICAL DEVICES AND METHODS OF MANUFACTURING SAME

FIELD

The present disclosure relates generally to medical devices, such as maneuverable guidewires, catheters and other elongate flexible members, used to access target sites in a mammalian vasculature. In particular, the present disclosure relates to fluid-sealed, slotted medical devices, such as guidewires, and methods for manufacturing same.

BACKGROUND

The use of intravascular guidewires, catheters and other types of elongate delivery members for accessing and treating various types of vascular disease is well-known. In general, a suitable intravascular guidewire, catheter or other delivery member inserted into the vascular system, e.g., via introduction through a femoral or jugular artery or vein, and navigated through the vasculature to a desired target site. By using an appropriately sized device having the requisite performance characteristics, such as "pushability" "steerability", "torquability" and most important, distal tip flexibility, virtually any target site in the vascular system may be accessed, including within the tortuous cerebral vasculature.

For example, balloon catheters are used in a number of endovascular applications, including for temporarily or permanently occluding blood flow either distal or proximal of a treatment site during neurological examinations, delivering diagnostic agents such as contrast media, assisting in neurovascular embolic coiling of an aneurysm or arteriovenous malformation (AVM), and dilating narrowed blood vessels caused by vasospasm. During therapeutic procedures such as the ones mentioned above, the distal ends of some balloon catheters are substantially sealed by a guidewire inserted into the catheter lumen for inflation of a balloon portion by pressurized inflation fluid. To facilitate a more complete and secure seal of the balloon portion against the distal end of the guidewire, the guidewire is preferably configured such that its outer diameter is substantially constant along its longitudinal axis. As used in this application, a "substantially constant" elongate member outer diameter is an outer diameter that varies less than about 20% from the average outer diameter along the elongate member's longitudinal axis.

Many medical devices, such as guidewires, incorporate slots into their construction. Incorporating slots into medical devices can modify or customize the device flexibility/stiffness, especially of elongate medical devices. Examples of slotted medical devices are described in U.S. Pat. No. 5,095,915, the entire disclosure of which is incorporated herein by reference, as though set forth in full.

More specifically, guidewires may include slotted metallic hypotubes. Such slotted hypotubes provide superior performance characteristics (i.e., pushability, steerability, torquability, and flexibility/stiffness) for accessing cerebral blood vessels. Further, slot patterns in guidewire tubular shafts can be varied to modify or customize the stiffness of various portions of guidewires. For instance, distal portions of guidewire shafts may have a slot pattern (e.g., more slots per area, longer slots, and/or wider slots) that decreases the stiffness thereof. When used as components of guidewires, the slotted hypotubes are preferably substantially sealed to prevent inflation fluids from entering into the inner lumen of the tube, and also to enhance lubricity. Exemplary slotted hypotubes are disclosed and described in U.S. Pat. Nos. 8,858,643 and 9,162,040, the entire disclosures of which are incorporated herein by reference, as though set forth in full.

Many medical devices are also coated to improve their functionality. For instance, some medical devices are coated with a lubricious polymer to reduce friction when the devices are inserted into catheters and body lumens. Coating slotted medical devices can also close the slots therein, render at least portions of the slotted medical devices fluid-tight. Examples of coated medical devices are described in U.S. Pat. Nos. 5,443,455 and 6,488,637, the entire disclosures of which are incorporated herein by reference, as though set forth in full.

Medical devices are coated using various methods, such as spray coating, dip coating, extrusion and lamination. Regardless of the coating method, variations in the slot volume (i.e., the total volume of slots formed in a longitudinal section per section length) of different regions of the slotted tube can result in different outer diameters in these regions, because the slots function as reservoirs or sinks for receiving a liquid coating material. Accordingly, varying slot patterns to modify the stiffness of various regions of guidewires may change the slot volume of those regions, and inadvertently vary the outer diameter of those regions. This can result in undesired effects, such as failure to substantially seal the distal ends of some balloon catheters and corresponding inflation fluid leakage and reduced balloon performance.

SUMMARY

In accordance with one aspect of the disclosed inventions, a method of forming a fenestrated tubular support member includes determining a first iso-stiffness curve corresponding to a first function of beam length versus ring width for the first stiffness; determining a second iso-stiffness curve corresponding to a second function of beam length versus ring width for the second stiffness; determining an iso-volume curve corresponding to a third function of beam length versus ring width for a given fenestration volume; identifying a first intersection point where the iso-volume curve intersects the first iso-stiffness curve; and identifying a second intersection point where the iso-volume curve intersects the second iso-stiffness curve. The first section ring width and first section beam length are determined from the first intersection point, and the second section ring width and second section beam length are determined from the second intersection point. The formed fenestrated tubular support member includes a first section having a first pattern of successive first section annular rings connected by respective first section axial beams, and a second section having a second pattern of successive second section annular rings connected by respective second section axial beams. Each of the first section annular rings has a first section ring width and each of the first section beams has a first section beam length. Each of the second section annular rings has a second section ring width and each of the second section beams has a second section beam length. The first section has a first stiffness and the second section has a second stiffness different than the first stiffness.

In accordance with another aspect of the disclosed inventions, a method of forming a fenestrated tubular support member includes determining a first iso-stiffness curve corresponding to a first function of beam length versus ring width for the first stiffness; determining a second iso-stiffness curve corresponding to a second function of beam length versus ring width for the second stiffness; determining a first iso-volume curve corresponding to a third function of beam length versus ring width for the first fenestration volume; determining a second iso-volume curve corresponding to a fourth function of beam length versus ring width for the second fenestration volume; identifying a first intersection point where the first iso-volume curve intersects the first iso-stiffness curve; and identifying a second intersection point where the second iso-volume curve intersects the second iso-stiffness curve. The first section ring width and first section beam length are determined from the first intersection point, and the second section ring width and second section beam length are determined from the second intersection point. The formed fenestrated tubular support member includes a first section having a first pattern of successive annular rings connected by respective axial beams, and a second section having a second pattern of successive annular rings connected by respective axial beams. Each of the first section annular rings has a first section ring width and each of the first section beams has a first section beam length. Each of the second section annular rings has a second section ring width and each of the second section beams has a second section beam length. The first section has a first stiffness and the second section has a second stiffness different than the first stiffness. The first section has a first fenestration volume, and the second section has a second fenestration volume different than the first fenestration volume.

In one or more embodiments, the method also includes forming the first and second patterns in respective first and second sections of a tube. Forming the first and second patterns comprises processing the respective first and second sections of the tube, and may include using micro-machining, laser-cutting, saw-cutting, electron discharge machining, grinding, milling, casting, molding, chemically etching, 3D printing or other additive methods.

In one or more embodiments, the method also includes applying a coating material to the first and second sections of the tube to form respective first and second coated sections of the tube. Applying the coating material comprises treating the respective first and second sections of the tube, and may include using spray coating, dip coating, extrusion or lamination. Forming the first and second patterns may include forming first fenestrations in the first section of the tube, and forming second fenestrations in the second section of the tube. Applying the coating material may include substantially filling the first and second fenestrations with the coating material.

In one or more embodiments, the coated first section has a first outer diameter, and the coated second section has a second outer diameter substantially the same as the first outer diameter. In other embodiments, the coated first section has a first outer diameter, and the coated second section has a second outer diameter different from first outer diameter.

In accordance with still other aspects of the disclosed inventions, a fenestrated tubular support member is formed by one of the above-described methods.

Other and further aspects and features of embodiments will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIG. 15 is a table summarizing characteristics of the tubular member sections depicted in FIGS. 5A to 14C.

DETAILED DESCRIPTION OF THE ILLUSTRATED EMBODIMENTS

Figure 1:
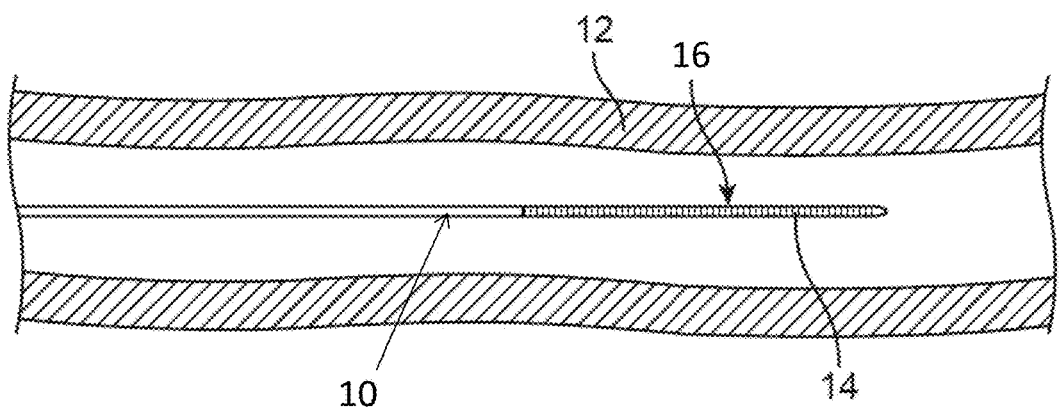
FIG. 1 is a plan view of a medical device constructed according to one embodiment and disposed in a vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this application, a "tubular member" is any elongate device having a lumen. The lumen may extend the entire length of the elongate device (i.e., from a first end to a second, opposite end), or the lumen may extend less than the entire length of the elongate device. A tubular member can be formed from any material, including, but not limited to, metals and polymers. Tubular members may be fenestrated (not fluid-tight). While the tubular members described herein have substantially circular cross-sectional geometry, tubular members may have any cross-sectional geometry, including one that changes along the longitudinal axis of the device. Therefore, uses of terms that connote circular geometry, such as "radius," "diameter," "circumference," and "annular," are illustrative, and not intended to be limiting. In embodiments not having substantially circular cross-sectional geometry, such term refer to their non-circular cross-section analogs. Accordingly, such terms are intended to include analogous concepts in tubular members having non-circular geometries.

As used in this application, a "cross-sectional plane" of a tubular member includes, but is not limited to, a plane normal to the longitudinal axis thereof.

As used in this application, a "ring width" of an annular segment/ring of a tubular member is the longitudinal (or axial) distance from a first side of the annular segment/ring along a longitudinal axis of the tubular member to a second, opposite side.

As used in this application, a "beam length" of a beam of a tubular member is the circumferential distance spanned by the beam between two slots or between two ends of one slot. In embodiments where the beam length changes along the radial thickness of the beam, the beam length is the circumferential distance spanned by the beam at the outer surface of the tubular member.

As used in this application, an "opening" or a "fenestration" in a tubular member is any space formed in or through the wall of the tubular member, including, but not limited to, spaces that penetrate the tubular member from an outer surface to an inner surface thereof, and spaces that do not penetrate the tubular member. For instance, fenestrations need not be largely circumferential slots, but could take a variety of shapes, such as those described in U.S. Pat. No. 9,227,037, the entire disclosure of which is herein incorporated by reference, as though set forth in full.

As used in this application, "slot depth" of a slot in a tubular member is the radial distance a slot extends into a tubular member. Slot depth has a maximum determined by the radial thickness of the tubular member. In slots with constant slot depth along the slot, the slot depth is equal to the dimension (as measured from an outer surface of the tubular member to an inner surface of the slot) of each of the flat walls at opposite circumferential ends of the slot. The slot depth may also vary along the slot. For instance, slots formed by substantially circular blades with small radii may have variable slot depths along the slot.

As used in this application, "slot length" of a slot in a tubular member is the circumferential length of the slot, as measured along the outside diameter of the tubular member. The slot length may be any value less than the outer circumference of the tubular member.

As used in this application, "slot width" of a slot is the longitudinal (or axial) distance between the two longitudinal surfaces defining the slot.

As used in this application, "slot spacing" of two longitudinally adjacent slots is the longitudinal (or axial) distance between the centerlines of the adjacent slots. In embodiments where (1) slots have a constant width, (2) the widths of adjacent slots are equal, and (3) adjacent slots are separated by one annular segment, slot spacing is equal to the ring width of the annular segment plus the slot width.

As used in this application, "beam centerline offset" of two beams that define a slot is the distance by which the centroid of the two beams is offset from the central axis of tubular member. In other words, the magnitude of the beam centerline offset is the length of the perpendicular line connecting the line between the midpoints of the two beams and a diameter of the circular cross-section of the tubular member parallel thereto, as shown in FIG. 9C and described below.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a plan view of a guidewire 10 according to one embodiment disposed in a blood vessel 12. Guidewire 10 includes a tubular member 14 (e.g., a slotted hypotube 14) disposed at a distal end 16 of the guidewire 10 and configured to modify the stiffness of the distal end 16 of the guidewire 10. The guidewire 10 also includes a coating (not shown) over at least a portion of the tubular member 14 and configured to facilitate delivery of the guidewire 10 into the blood vessel 12. Guidewire 10 may be used for various intravascular procedures. For example, guidewire 10 may be used to seal the distal end of a balloon catheter (not shown). Alternatively, guidewire 10 may be used with a delivery catheter (not shown) to deliver a stent (not shown) to treat and/or diagnose a medical condition.

Figure 2A:
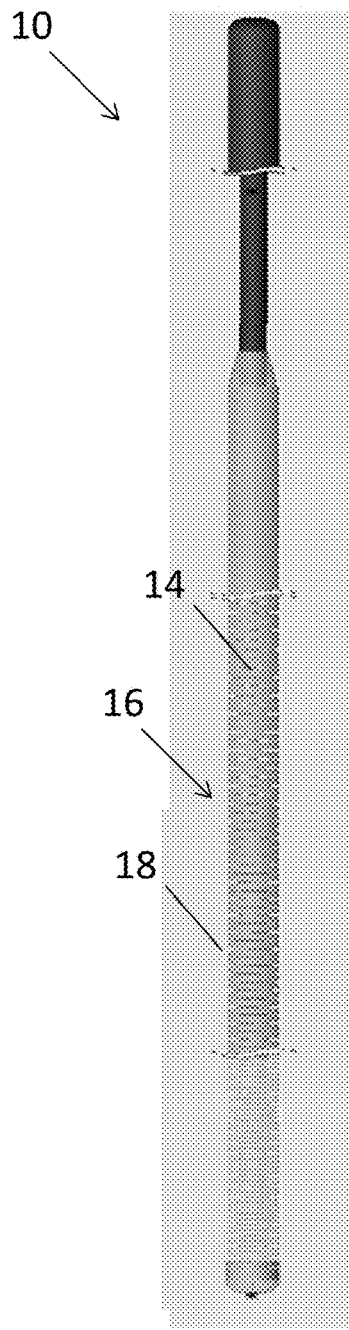
FIG. 2A is a detailed plan view of a medical device constructed according to another embodiment.
Figure 2B:
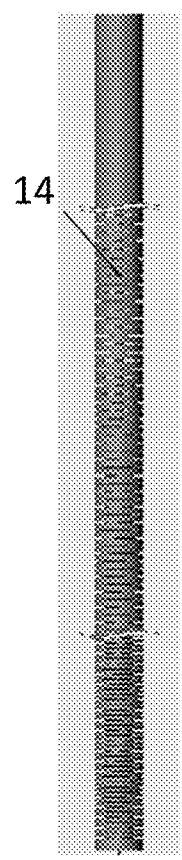
FIG. 2B is a detailed plan view of the tubular member of the medical device in FIG. 2A.

FIG. 2A is a detailed plan view of a guidewire 10 according to another embodiment. The guidewire 10 includes a tubular member 14 (e.g., a slotted hypotube 14) at a distal end 16 thereof. The tubular member 14 is covered by a coating 18. The coating can be a polymer, such as polyurethane (e.g., a laminated TECOFLEX tube). FIG. 2B is a detailed plan view of the tubular member 14 of the guidewire 10 depicted in FIG. 2A. The tubular member 14 is shown in FIG. 2B without the coating 18.

Figure 3:
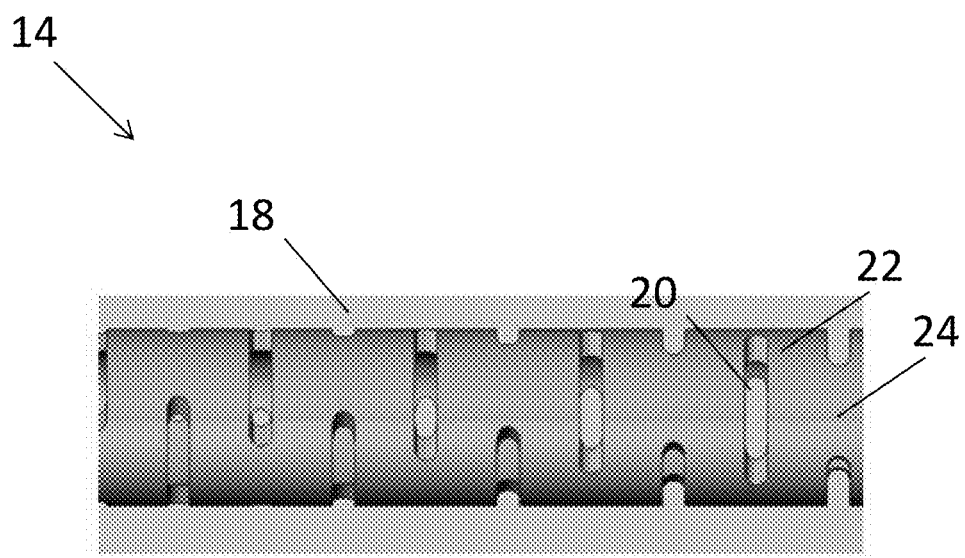
FIG. 3 is a side view of a tubular member section according to one embodiment.

FIG. 3 is a side view of a tubular member 14 section, e.g., a slotted hypotube 14 section, according to still another embodiment. The slotted hypotube 14 defines a plurality of openings 20 therein. In the depicted slotted hypotube 14, the openings 20 are elongated slots 20 that extend circumferentially and substantially perpendicular to the longitudinal axis of slotted hypotube 14. As a result of segmentation by the slots 20, the slotted hypotube 14 is generally a stack of annular segments (i.e., rings) 22 connected by a plurality of beams 24. In the slotted hypotube 14 depicted in FIG. 3, the annular segments 22 are substantially perpendicular to the longitudinal axis of the slotted hypotube 14 and the beams 24 are substantially parallel to the longitudinal axis of slotted hypotube 14. The slotted hypotube 14 also includes an optional coating 18, as described above.

The slots 20 depicted in FIG. 3 penetrate the full radial thickness of the slotted hypotube 14. All slots 20 formed in a hypotube 14 with a circular cross-section perpendicular to a longitudinal axis thereof will be arcuate when viewed from an axial direction (as shown in e.g., FIG. 5C) because the hypotube 14 forms a circle when viewed from an axial direction.

Slots can be formed in hypotubes by saw-cutting with circular blades. Other types of cutting systems include, but are not limited to, laser cutting, electric discharge machining and plasma arc cutting systems. In other embodiments, slotted hypotubes are manufactured using "additive" manufacturing (e.g., 3D printing) rather than the various "subtractive" techniques listed.

In embodiments where the slots do not penetrate the full radial thickness of the slotted hypotube (not shown), the slots also have slot bases. Slot bases may be flat or arcuate. For instance, slots made with circular blades having diameters substantially larger than the diameter of the hypotube may have slot bases that are essentially flat. On the other hand, slots made using saw-cutting with circular blades having diameters about the same size as the diameter of the hypotube may have arcuate slot bases.

Figure 4:
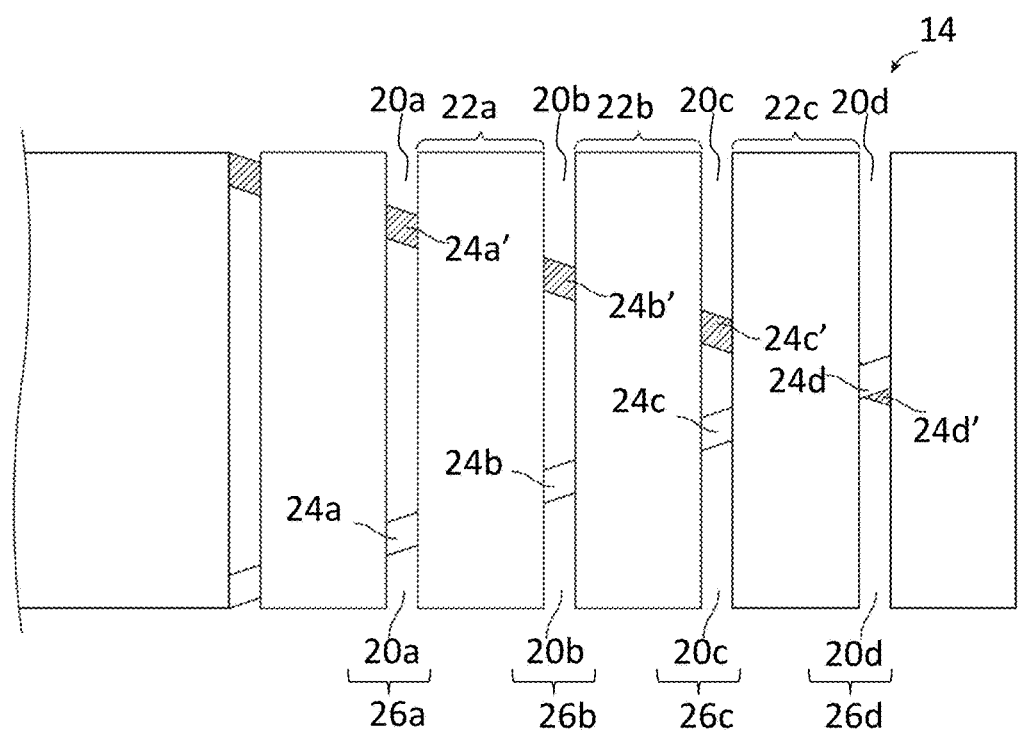
FIG. 4 is a detailed side view of a tubular member section according to another embodiment.

FIG. 4 is a side view of a tubular member 14 (e.g., a slotted hypotube 14). Tubular member 14 includes a plurality of annular segments 22 including annular segment 22a, annular segment 22b, and annular segment 22c. In this example, segment 22a is disposed longitudinally-adjacent (i.e., right next to) segment 22b and segment 22c is disposed longitudinally-adjacent segment 22b (oppositely segment 22a). The number of annular segments 22 in a given tubular member 14 may vary depending on the structure of tubular member 14. For example, as the number of openings 20 increases, the number of annular segments 22 may similarly increase.

Segments 22a/22b/22c can be understood to be generally circumferential or "round" portions of tubular member 14 that are defined between groups or sets 26 (in this case, pairs) of openings 20 that are generally aligned in a plane orthogonal to the longitudinal axis of the tubular member 14. For example, segment 22a is defined between a first group 26a of openings 20a and a second group 26b of openings 20b. Likewise, segment 22b is defined between the second group 26b of openings 20b and a third group 26c of openings 20c. Moreover, segment 22c is defined between the third group 26c of openings 20c and a fourth group 26d of openings 20d. In this example, each group 26a/26b/26c/26d includes two openings 20. However, any suitable number of openings 20 may be utilized for any group 26a/26b/26c/26d. The tubular member 14 may include any number of openings 20, groups 26 of openings 20, or number of openings 20 per group 26 for any given tubular member 14 or device including a tubular member 14 with openings 20.

When openings 20 are formed in the tubular member 14, a portion of tubular member 14 remains at the longitudinal location where openings 20 are formed and extends between longitudinally-adjacent annular segments 22. This portion is called a "beam" 24. Several beams 24 are illustrated in FIG. 4 including beam 24a, beam 24a', beam 24b, beam 24b', beam 24c, beam 24c', beam 24d, and beam 24d'. Beams 24a/24a'/24b/24b'/24c/24c'/24d/24d' can be understood to be portions of tubular member 14 that connects or attaches longitudinally-adjacent annular segments 22. Each pair of longitudinally-adjacent annular segments (e.g., 22a and 22b) is attached by two beams (e.g., 24b and 24b'), which form a beam pair at the same longitudinal location along tubular member 14. Similarly, segment 22b is attached to segment 22c by beams 24c and 24c'. In this example, each group 26a/26b/26c/26d of openings 20 defines or leaves behind two, corresponding beams 24a,24a'/24b,24b'/24c,24c'/24d, 24d' at the respective longitudinal location. In FIG. 4, which illustrates tubular member 14 from the side, one beam (e.g., 24a, 24b, 24c, 24d) of each beam pair can be seen from the front and the other beam (e.g., 24a', 24b', 24c', 24d') of the beam pair can be seen from the back and is shaded for clarity. While the beams 24 depicted in FIG. 4 are not parallel to the longitudinal axis of the tubular device 14, the beams 24 can be parallel to the longitudinal axis in other tubular devices 14, as shown in e.g., FIG. 5A.

Figure 5A:
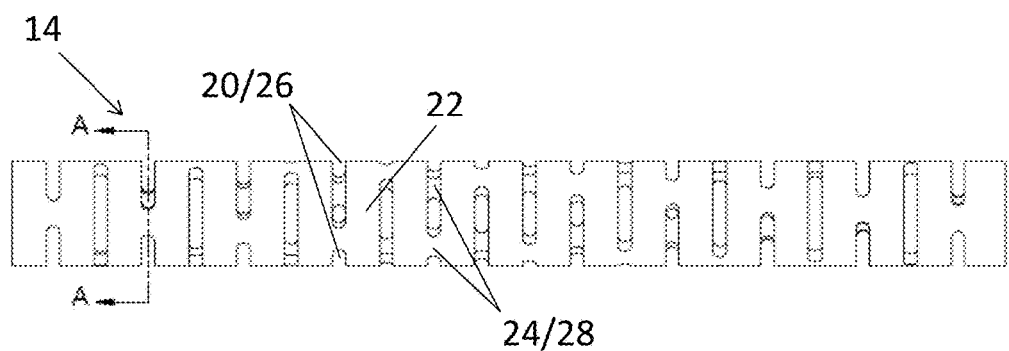
FIGS. 5A, 6A, 7A, 8A, 9A, 10A, 11A, 12A, 13A and 14A are detailed side views of tubular member sections according to various embodiments.

In various embodiments of tubular members 14, different arrangements and configurations of openings 20, annular segments 22, and beams 24 are contemplated. In some embodiments, at least some, if not all of the beams 24 are disposed such that their respective longitudinal axes form a same angle or similar angles (e.g., 0 degrees or substantially parallel as shown in FIG. 5A) with the longitudinal axis of the guidewire 10. In other embodiments, the beams 24 are disposed such that their respective longitudinal axes form different angles with the longitudinal axis of the guidewire 10. In a similar manner, tubular members 14 can be formed according to various embodiments such that some or all of the annular segments 22 and beams 24 have various geometries relative to the longitudinal axis of the guidewire 10. Further, tubular members 14 according to these embodiments will have openings 20 with various geometries, because the openings 20 are defined by the annular segments 22 and beams 24, i.e., the portions of the tubular member 14 remaining after openings 20 are formed therein. The distribution and/or configuration of the openings 20, annular segments 22, and beams 24 can include, to the extent applicable, any of those disclosed in U.S. Pat. Nos. 7,878, 984 and 9,227,037, the entire disclosures of which is herein incorporated by reference, as though set forth in full.

Openings 20 enhance the flexibility of the tubular member 14 while the beams 24 and annular segments 22 retain suitable torque transmission characteristics. Openings 20 are formed such that the annular segments 22 are interconnected by one or more beams 24. Such an interconnected structure displays a relatively high degree of torsional stiffness, while retaining a desired level of lateral (i.e., orthogonal relative to the longitudinal axis) flexibility. In some embodiments, some adjacent openings 20 can be formed such that they include portions that overlap (when viewed axially) with each other to some degree about the circumference of tubular member 14. In other embodiments, some adjacent openings 20 can be disposed such that they do not necessarily overlap with each other, but are disposed in a pattern that provides the desired degree of lateral flexibility.

Additionally, openings 20 can be arranged along the length of, or about the circumference of, tubular member 14 to achieve desired properties. For example, adjacent openings 20, or groups of openings 20, can be arranged in a symmetrical pattern, such as being disposed essentially equally on opposite sides about the circumference of tubular member 14, or can be rotated by an angle relative to each other about the axis of tubular member 14. Additionally, adjacent openings 20, or groups of openings 20, may be equally spaced along the length of tubular member 14, or can be arranged in an increasing or decreasing density pattern, or can be arranged in a non-symmetric or irregular pattern. Other characteristics, such as opening size, opening shape and/or opening angle with respect to the longitudinal axis of tubular member 14, can also be varied along the length of tubular member 14 in order to vary the flexibility/ stiffness or other properties. In other embodiments, moreover, it is contemplated that the portions of the tubular member may not include any such openings 20.

As suggested above, openings 20 may be formed in groups of two, three, four, five, or more openings 20, which may be located at substantially the same longitudinal location along the axis of tubular member 14. Alternatively, a single opening 20 may be disposed at some or all of these longitudinal locations. Within the groups of openings 20, there may be included openings 20 that are equal in size (i.e., span the same circumferential distance around tubular member 14). In some of these as well as other embodiments, at least some openings 20 in a group are unequal in size (i.e., span a different circumferential distance around tubular member 14). Longitudinally adjacent groups of openings 20 may have the same or different configurations.

For example, some embodiments of tubular members 14 include openings 20 that are equal in size in a first group and then unequally sized in an adjacent group. It can be appreciated that in groups that have two openings 20 that are equal in size and are symmetrically disposed around the tube circumference, the centroid of the pair of beams 24 is coincident with the central axis of tubular member 14. Conversely, in groups that have two openings 20 that are unequal in size and whose beams 24 are directly opposed on the tube circumference, the centroid of the pair of beams 24 is offset from the central axis of tubular member 14. Some embodiments of tubular member 14 include only slot groups with centroids that are coincident with the central axis of the tubular member 14, only slot groups with centroids that are offset from the central axis of tubular member 14, or slot groups with centroids that are coincident with the central axis of tubular member 14 in a first group and offset from the central axis of tubular member 14 in another group. The amount of offset may vary depending on the depth (or length) of openings 20 and can include essentially any suitable distance.

Openings 20 can be formed by methods such as micromachining, laser-cutting, saw-cutting (e.g., using a diamond grit embedded semiconductor dicing blade), electron discharge machining, grinding, milling, casting, molding, chemically etching or treating, 3D printing, or other known methods, and the like. In some such embodiments, the structure of the tubular member 14 is formed by cutting and/or removing portions of the tube to form openings 20. Some example embodiments of appropriate micromachining methods and other cutting methods, and structures for tubular members including slots and medical devices including tubular members are disclosed in U.S. Pat. Publication No. 2003/0069522, and U.S. Pat. Nos. 6,766,720, 6,579,246, 7,879,894, and 9,227,037, the entire disclosures of which are herein incorporated by reference, as though set forth in full. Some example embodiments of etching processes are described in U.S. Pat. No. 5,106,455, the entire disclosure of which is herein incorporated by reference, as though set forth in full. It should be noted that the methods for manufacturing balloon catheter 10 may include forming openings 20 in tubular member 14 using any of these or other manufacturing steps.

In at least some embodiments, openings 20 may be formed in tubular members using a laser cutting process. The laser cutting process may include essentially any suitable laser and/or laser cutting apparatus. For example, the laser cutting process may utilize a fiber laser. Utilizing processes like laser cutting may be desirable for a number of reasons. For example, laser cutting processes may allow tubular member 14 to be cut into a number of different cutting patterns in a precisely controlled manner. This may include variations in the slot width (which also may be termed "kerf"), annular segment width, beam height, beam width, beam length, etc. Further, changes to the cutting pattern can be made without the need to replace the cutting instrument (e.g., a blade). Consequently, tubular members 20 may be fabricated for use in neurological devices or other devices where a small size may be desired. Because of the precision and control that may be achieved by cutting openings 20 with a laser, numerous additional variations can be achieved in opening 20, annular segment 22, and beam 24 geometry, configuration, arrangement, etc.

In various embodiments, the tubular member 14 includes a first section 14a and a second section 14b. The first section 14a has first features including, but not limited to, openings 20, annular segments 22, and beams 24. The geometry of the first features results in the first section 14a having a first stiffness and a first "opening volume" or "fenestration volume." As used in this application, the "slot volume," "opening volume" or "fenestration volume" of a tubular member 14 means the total volume of open spaces or fenestrations in the wall of a tubular member 14 per unit of length (e.g., $in^3/in$). The second section 14b has second features including, but not limited to, openings 20, annular segments 22, and beams 24. The geometry of the second features results in the second section 14b having a second stiffness and a second opening volume. First and second features of the first and second sections 14a, 14b, can also include, but are not limited to, ring width, beam length, slot length, slot width, slot depth, beam centerline offset, number of slots in a cross-sectional plane, and the presence/absence/number of recesses that do not fully penetrate the wall of the tubular member (all described below).

In various embodiments, the tubular member 14 is configured to form part of a guidewire 10 such that the first section 14a is proximal of the second section 14b when the guidewire 10 is inserted into a body lumen. In some embodiments, the first stiffness may be greater than the second stiffness, such that the second section 14b, which is closer to the distal end of tubular member 14 and the guidewire 10, is more flexible. This modifies the guidewire 10 so that its distal end is more flexible than its proximal end, thereby facilitating navigation through tortuous and narrowing body lumens.

Simultaneously, the first opening volume and the second opening volume are substantially similar. As used in this application, "substantially similar" opening volumes vary from each other by less than about 10%. Because the first and second sections 14a, 14b have substantially similar opening volumes, when a coating 18 is applied to the first and second sections 14a, 14b of the tubular member 14, the outer diameter of the coated tubular member 14 remains substantially constant.

During one exemplary coating process, a substantially similar amount of coating material is applied to each longitudinal section of the tubular member 14 (e.g., first and second sections 14a, 14b). The coating material flows into the openings in each section of the tubular member 14. Therefore, the thickness of the coating 18 outside of each section of the tubular member 14, which affects the outer diameter of each section of the coated tubular member 14, is inversely related to the opening volume of each section of the tubular member 14. Consequently, maintaining substantially similar first and second opening volumes in the first and section tubular member sections 14a, 14b also maintains a substantially constant outer diameter in the first and tubular member section sections 14a, 14b, and the guidewire 10 in which they are incorporated. Having a substantially constant guidewire outer diameter improves the guidewire's ability to perform various functions, such as sealing a balloon catheter and insertion through tortuous vessels.

Figure 5B:
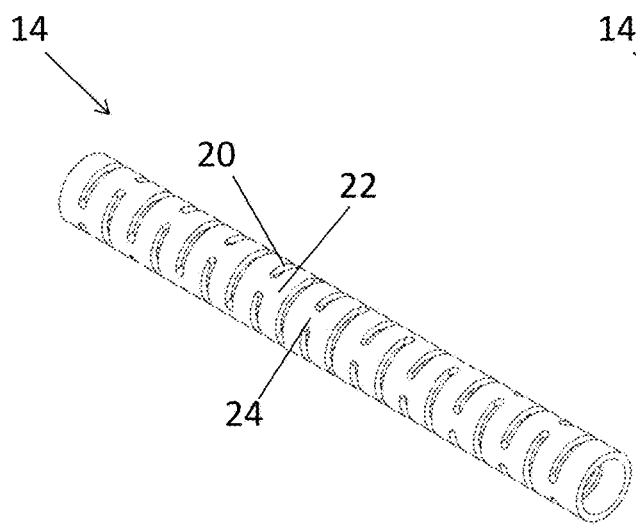
FIGS. 5B, 6B, 7B, 8B, 9B, 10B, 11B, 12B and 13B are detailed perspective views of the tubular member sections depicted in FIGS. 5A, 6A, 7A, 8A, 9A, 10A, 11A, 12A and 13A, respectively.
Figure 5C:
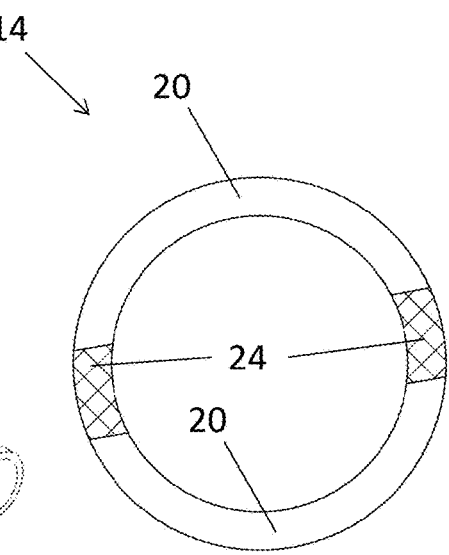
FIGS. 5C, 6C, 7C, 8C, 9C, 10C, 11C, 12C, 13C and 14B are axial cross-sectional views of the tubular member sections depicted in FIGS. 5A, 6A, 7A, 8A, 9A, 10A, 11A, 12A, 13A and 14A through respective lines labeled A-A in the corresponding side view (i.e., "A") figures.

FIGS. 5A-5C depict a section of a tubular member 14 according to one embodiment. The tubular member 14 section includes a plurality of annular segments/rings 22 connected sequentially by a corresponding plurality of groups (i.e., pairs) 28 of beams 24. FIGS. 5A and 5B are side and perspective views, respectively. FIG. 5C is an axial cross-sectional view along the line labeled A-A in FIG. 5A.

As shown in FIG. 5C, the beams 24 of each pair 28 are disposed in the same longitudinal/axial plane, and on opposite sides of the tubular member 14 from each other. Each beam 24 of each pair 28 has flat walls at opposite circumferential ends of the beam 24, because the beam 24 is formed using a method (e.g., saw-cutting using blades with large diameters) that results in flat walls. The wall of the two beams 24 can be formed with two cuts.

The annular segments 22 and pairs 28 of beams 24 define a plurality of slots 20 along the length of the tubular member 14 segment. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of the tubular member 14 segment every approximately 72 pairs 28 of beams 24. Because the structure is symmetrical about the longitudinal axis, the structure gives the appearance of a complete rotation every 36 beam pairs.

The circumferential length of each beam 24 in this example is approximately 0.0030 in. Also, the longitudinal width of each slot 20 is approximately 0.00157 in. Further, the longitudinal spacing between each pair of adjacent slots 20 is approximately 0.00557 in. The longitudinal width of each ring 22 is equal to the longitudinal spacing of the slots minus the slot width, or 0.004 ins in this example. The resulting tubular member 14 section has a flexural rigidity ("EI") of $1.51 \times 10^{-4}$ in$^2$/lb. These characteristics and properties are summarized in the table in FIG. 15. All of the EI values in FIG. 15 (i.e., for the embodiments depicted in FIGS. 5-14) are calculated using the following tube characteristics:

Outer Diameter=0.0122 in.
Inner Diameter=0.0097 in.
Young's Modulus ("E") of Tube Material NiTi≈8.5E6 P.S.I.

Number of Beams Per Group

Figure 6A:
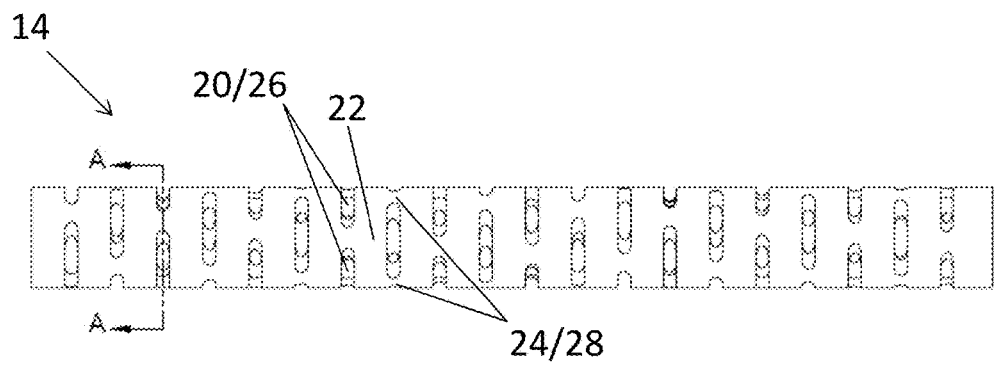
Figures 6B, 6C:
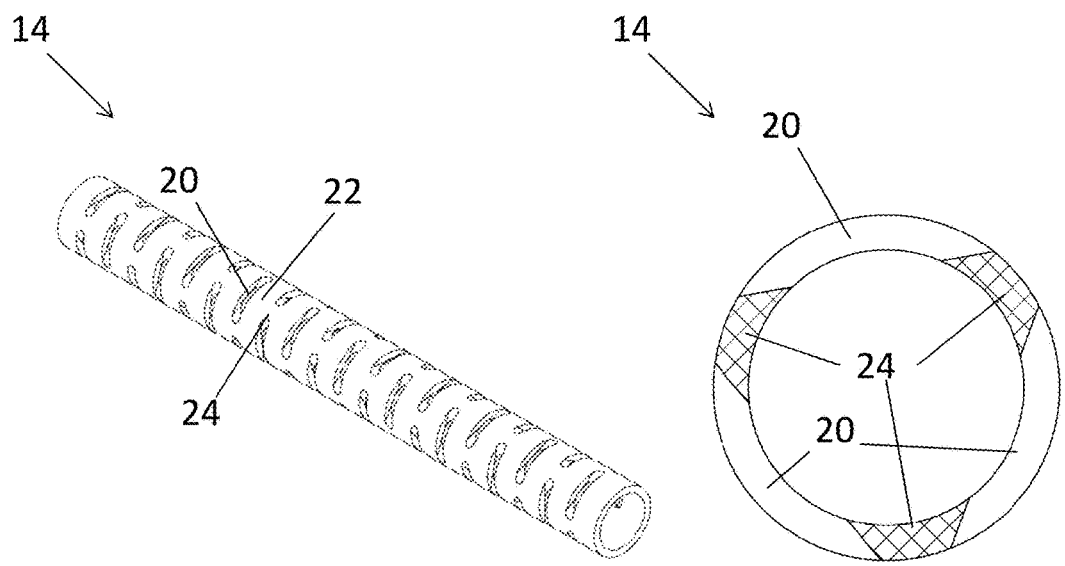

FIGS. 6A-6C depict a section of a tubular member 14 according to another embodiment. The tubular member 14 section includes a plurality of annular segments/rings 22 connected sequentially by a corresponding plurality of groups (i.e., triplets) 28 of beams 24. FIGS. 6A and 6B are side and perspective views, respectively. FIG. 6C is an axial cross-sectional view along the line labeled A-A in FIG. 6A.

As shown in FIG. 6C, the beams 24 of each triplet 28 are disposed in the same longitudinal/axial plane, with the center of each beam 24 approximately 120 degrees displaced from the centers of the other beams 24. Each beam 24 of each triplet 28 has flat walls at opposite circumferential ends of the beam 24, because the beam 24 is formed using a method (e.g., saw-cutting using blades with large diameters) that results in flat walls. The wall of the three beams 24 can be formed with three cuts.

The annular segments 22 and triplets 28 of beams 24 define a plurality of slots 20 along the length of the tubular member 14 segment. Longitudinally adjacent triplets 28 of beams 24 are rotated relative to each other (about the longitudinal axis) by about 55 degrees, such that a particular beam 24 of the triplet 28 appears to make a complete (360 degree) rotation about the longitudinal axis of the tubular member 14 segment every approximately 72 triplets 28 of beams 24.

The circumferential length of each beam 24 is approximately 0.0025 in. Also, the longitudinal width of each slot 20 is approximately 0.00157 in. Further, the longitudinal spacing between each triplet of adjacent slots 20 is approximately 0.00557 in. The longitudinal width of each ring 22 is equal to the longitudinal spacing of the slots minus the slot width, or 0.004 ins in this example.

The resulting tubular member 14 section has an EI of $9.52 \times 10^4$ in$^2$/lb. These characteristics and properties are summarized in the table in FIG. 15. Comparing the characteristics and properties of the tubular member 14 sections depicted in FIGS. 5A-5C and FIGS. 6A-6C, and summarized in FIG. 15, demonstrates that EI can be increased with a larger number (e.g., from two to three per group 28) of smaller beams 24 (e.g., beam length from approximately 0.0030 in to approximately 0.0025 in). Of course, there are numerous other design options that increase EI (or decrease EI). Some of these are described below.

Beam Length

Figure 7A:
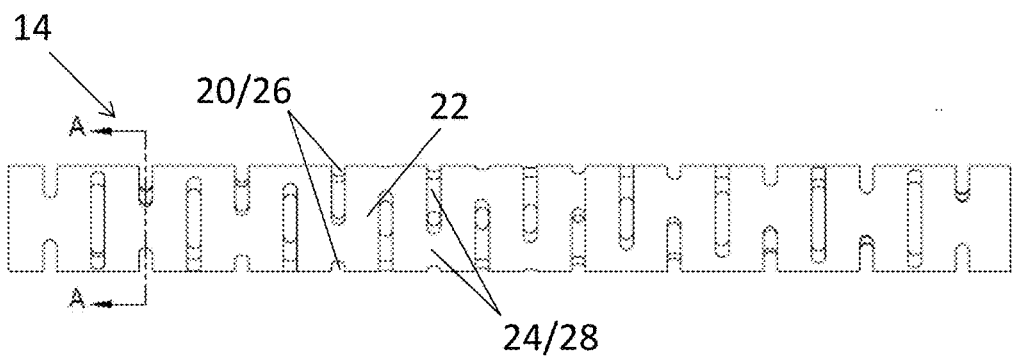
Figures 7B, 7C:
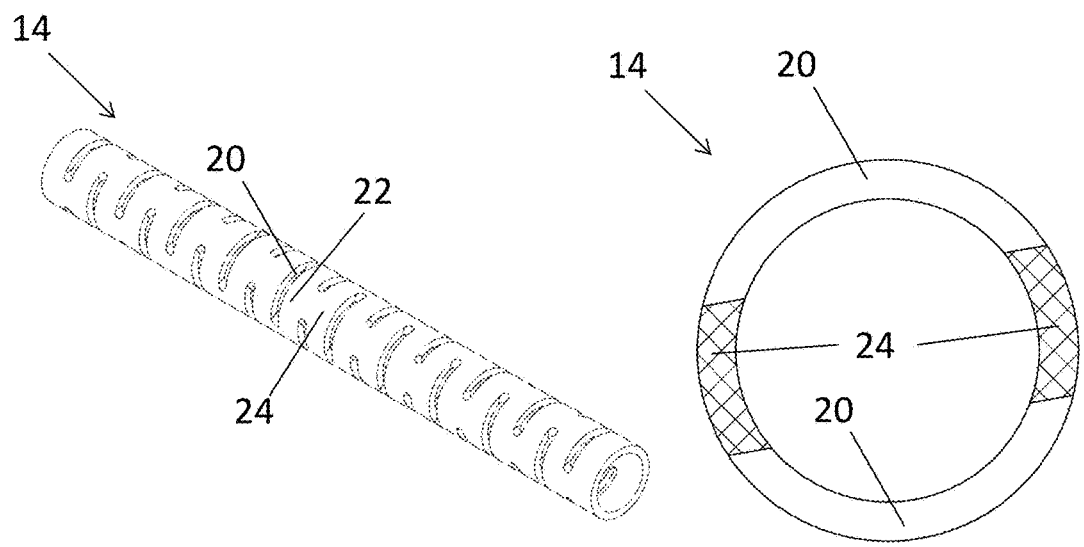

FIGS. 7A-7C depict a section of a tubular member 14 according to still another embodiment. The tubular member 14 section includes a plurality of annular segments/rings 22 connected sequentially by a corresponding plurality of groups (i.e., pairs) 28 of beams 24. FIGS. 7A and 7B are side and perspective views, respectively. FIG. 7C is an axial cross-sectional view along the line labeled A-A in FIG. 7A.

As shown in FIG. 7C, the beams 24 of each pair 28 are disposed in the same longitudinal/axial plane, with the center of each beam 24 approximately 180 degrees displaced from the centers of the other beams 24. Each beam 24 of each pair 28 has flat walls at opposite circumferential ends of the beam 24, because the beam 24 is formed using a method (e.g., saw-cutting using blades with large diameters) that results in flat walls. The walls of the two beams 24 can be formed with two cuts.

The annular segments 22 and pairs 28 of beams 24 define a plurality of slots 20 along the length of the tubular member 14 segment. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of the tubular member 14 segment every approximately 72 pairs 28 of beams 24.

The circumferential length of each beam 24 is approximately 0.0050 in. Also, the longitudinal width of each slot 20 is approximately 0.00157 in. Further, the longitudinal spacing between each pair of adjacent slots 20 is approximately 0.00557 in. The longitudinal width of each ring 22 is equal to the longitudinal spacing of the slots minus the slot width, or 0.004 ins in this example. The resulting tubular member 14 section has an EI of $3.90 \times 10^{-4}$ in$^2$/lb. These characteristics and properties are summarized in the table in FIG. 15. Comparing the characteristics and properties of the tubular member 14 sections depicted in FIGS. 5A-5C and FIGS. 7A-7C, and summarized in FIG. 15, demonstrates that EI can be increased by increasing beam 24 length (e.g., from 0.0030 in to 0.0050 in; compare FIGS. 5C and 7C), which results in smaller slot lengths.

Slot Spacing

Figure 8A:
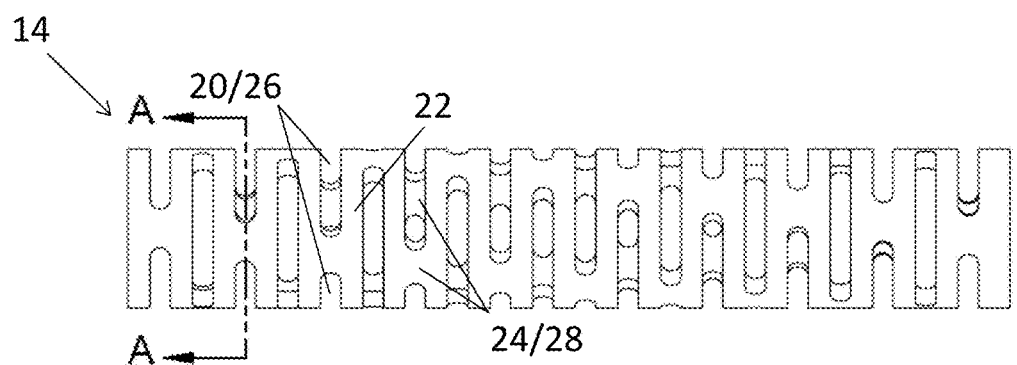
Figures 8B, 8C:
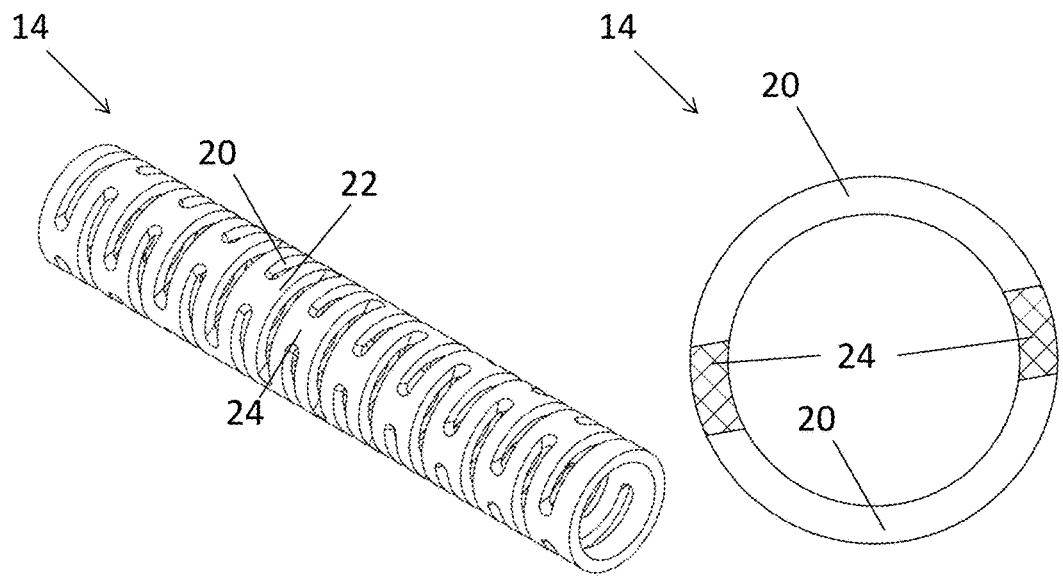

FIGS. 8A-8C depict a section of a tubular member 14 according to yet another embodiment. The tubular member 14 section includes a plurality of annular segments/rings 22 connected sequentially by a corresponding plurality of groups (i.e., pairs) 28 of beams 24. FIGS. 8A and 8B are side and perspective views, respectively. FIG. 8C is an axial cross-sectional view along the line labeled A-A in FIG. 8A.

As shown in FIG. 8C, the beams 24 of each pair 28 are disposed in the same longitudinal/axial plane, with the center of each beam 24 approximately 180 degrees displaced from the centers of the other beams 24. Each beam 24 of each pair 28 has flat walls at opposite circumferential ends of the beam 24, because the beam 24 is formed using a method (e.g., saw-cutting using blades with large diameters) that results in flat walls. The wall of the two beams 24 can be formed with two cuts.

The annular segments 22 and pairs 28 of beams 24 define a plurality of slots 20 along the length of the tubular member 14 segment. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of the tubular member 14 segment every approximately pairs 28 of beams 24.

The circumferential length of each beam 24 is approximately 0.0030 in. Also, the longitudinal width of each slot 20 is approximately 0.00157 in. Further, the longitudinal spacing between each pair of adjacent slots 20 is approximately 0.00327 in. The longitudinal width of each ring 22 is equal to the longitudinal spacing of the slots minus the slot width, or 0.0017 ins in this example. The resulting tubular member 14 section has an EI of $3.44 \times 10^{-5}$ in$^2$/lb. These characteristics and properties are summarized in the table in FIG. 15. Comparing the characteristics and properties of the tubular member 14 sections depicted in FIGS. 5A-5C and FIGS. 8A-8C, and summarized in FIG. 15, demonstrates that EI can be decreased by decreasing slot 20 spacing (e.g., from 0.00557 in to 0.00327 in), which also results in smaller ring width.

Centerline Offset

Figure 9A:
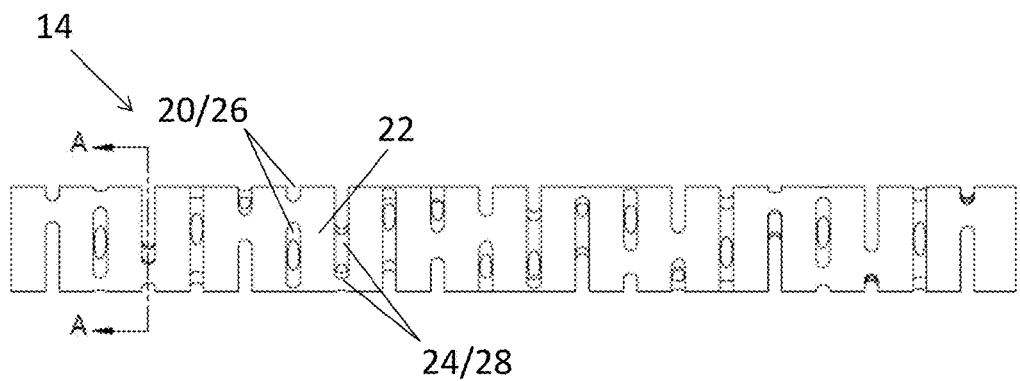
Figures 9B, 9C:
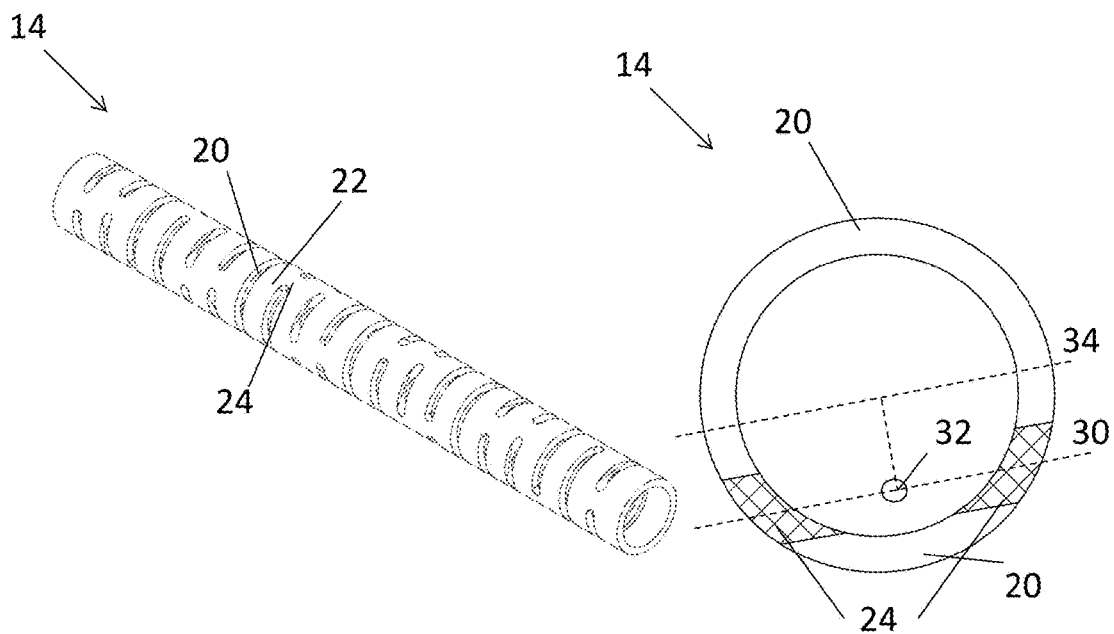

FIGS. 9A-9C depict a section of a tubular member 14 according to another embodiment. The tubular member 14 section includes a plurality of annular segments/rings 22 connected sequentially by a corresponding plurality of groups (i.e., pairs) 28 of beams 24. FIGS. 9A and 9B are side and perspective views, respectively. FIG. 9C is an axial cross-sectional view along the line labeled A-A in FIG. 9A.

As shown in FIG. 9C, the beams 24 of each pair 28 are disposed in the same longitudinal/axial plane, with the centers of the beams 24 forming a line 30 ("centerline"), which includes a centroid 32 of the beams 24, and is displaced from a parallel diameter 34 of the circular cross-section of the tubular member 14 section by approximately 0.0035 in. Each beam 24 of each pair 28 has flat walls at opposite circumferential ends of the beam 24, because the beam 24 is formed using a method (e.g., saw-cutting using blades with large diameters) that results in flat walls. The wall of the two beams 24 can be formed with two cuts.

The annular segments 22 and pairs 28 of beams 24 define a plurality of slots 20 along the length of the tubular member 14 segment. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of the tubular member 14 segment every approximately 72 pairs 28 of beams 24.

The circumferential length of each beam 24 is approximately 0.0030 in. Also, the longitudinal width of each slot 20 is approximately 0.00157 in. Further, the longitudinal spacing between each pair of adjacent slots 20 is approximately 0.00557 in. The longitudinal width of each ring 22 is equal to the longitudinal spacing of the slots minus the slot width, or 0.004 ins in this example. The resulting tubular member 14 section has an EI of $7.98 \times 10^{-5}$ in$^2$/lb. These characteristics and properties are summarized in the table in FIG. 15. Comparing the characteristics and properties of the tubular member 14 sections depicted in FIGS. 5A-5C and FIGS. 9A-9C, and summarized in FIG. 15, demonstrates that EI can be decreased by increasing the centroid/centerline offset (e.g., from 0.0000 in to 0.0035 in).

Slot Width

Figure 10A:
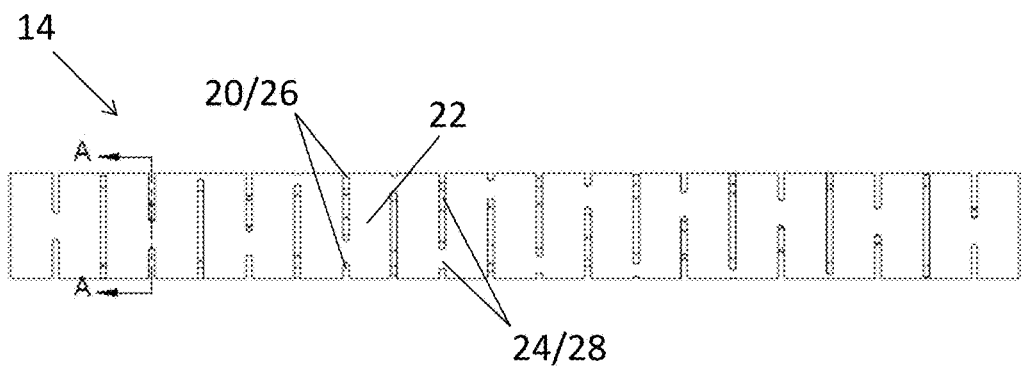
Figure 10B:
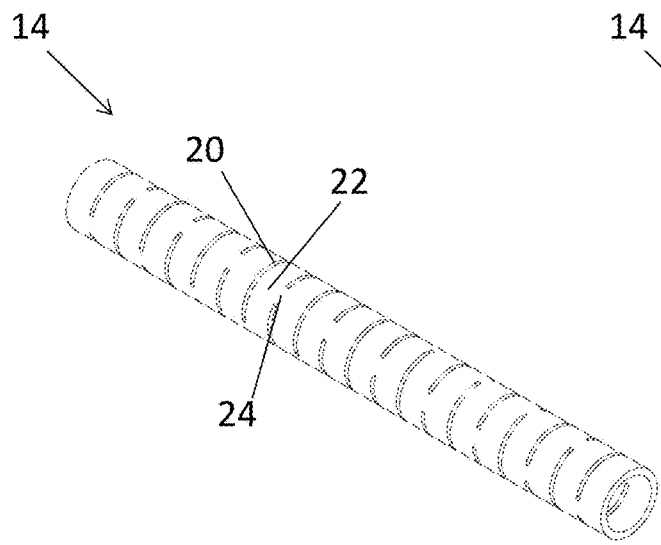
Figure 10C:
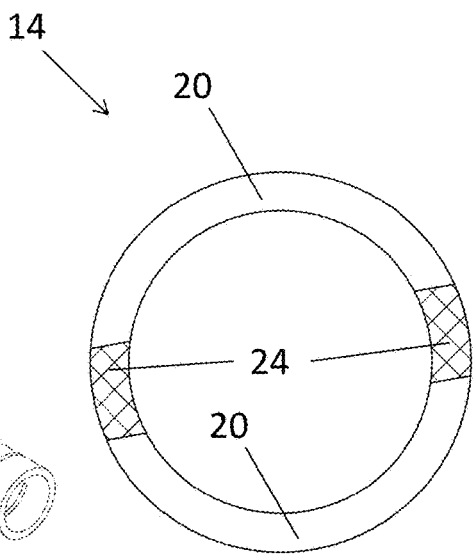

FIGS. 10A-10C depict a section of a tubular member 14 according to still another embodiment. The tubular member 14 section includes a plurality of annular segments/rings 22 connected sequentially by a corresponding plurality of groups (i.e., pairs) 28 of beams 24. FIGS. 10A and 10B are side and perspective views, respectively. FIG. 10C is an axial cross-sectional view along the line labeled A-A in FIG. 10A.

As shown in FIG. 10C, the beams 24 of each pair 28 are disposed in the same longitudinal/axial plane, with the center of each beam 24 approximately 180 degrees displaced from the centers of the other beams 24. Each beam 24 of each pair 28 has flat walls at opposite circumferential ends of the beam 24, because the beam 24 is formed using a method (e.g., saw-cutting using blades with large diameters) that results in flat walls. The wall of the two beams 24 can be formed with two cuts.

The annular segments 22 and pairs 28 of beams 24 define a plurality of slots 20 along the length of the tubular member 14 segment. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of the tubular member 14 segment every approximately 72 pairs 28 of beams 24.

The circumferential length of each beam 24 is approximately 0.0030 in. Also, the longitudinal width of each slot 20 is approximately 0.00070 in. Further, the longitudinal spacing between each pair of adjacent slots 20 is approximately 0.00557 in. The longitudinal width of each ring 22 is equal to the longitudinal spacing of the slots minus the slot width, or 0.00487 ins in this example. The resulting tubular member 14 section has an EI of $1.79 \times 10^{-4}$ in$^2$/lb. These characteristics and properties are summarized in the table in FIG. 15. Comparing the characteristics and properties of the tubular member 14 sections depicted in FIGS. 5A-5C and FIGS. 10A-10C, and summarized in FIG. 15, demonstrates that EI can be increased by decreasing slot 20 width (e.g., from 0.00157 in to 0.00070 in; compare FIGS. 5C and 10C).

Non-Penetrating Slots

Figure 11A:
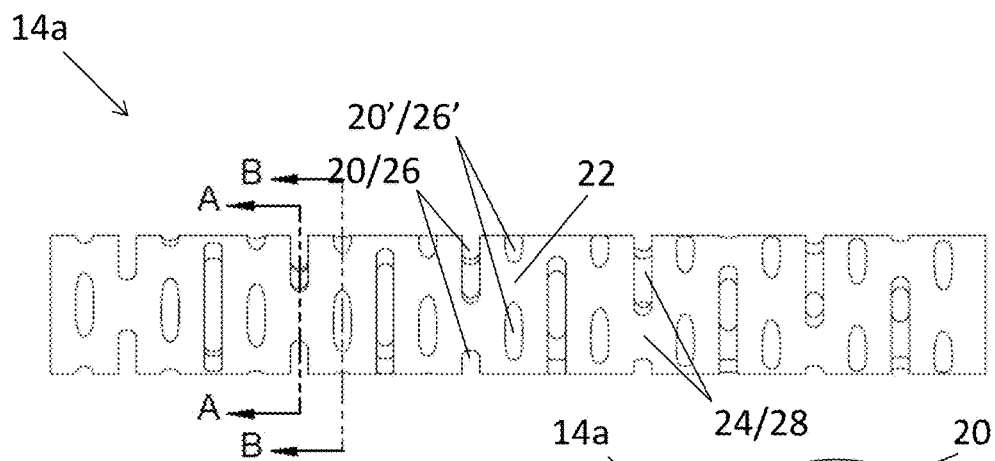
Figure 11B:
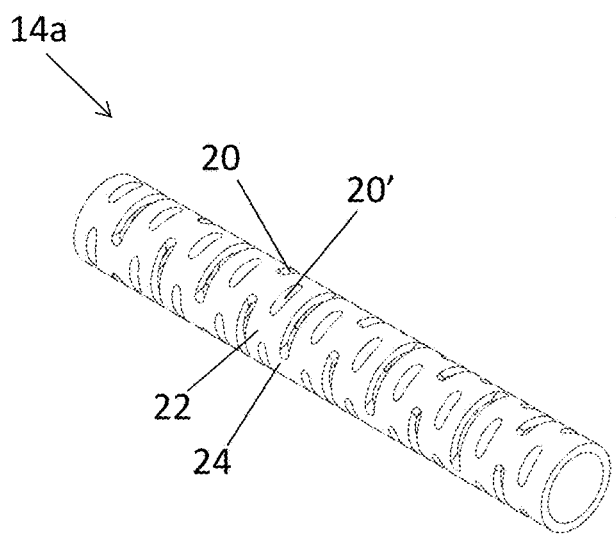
Figure 11C:
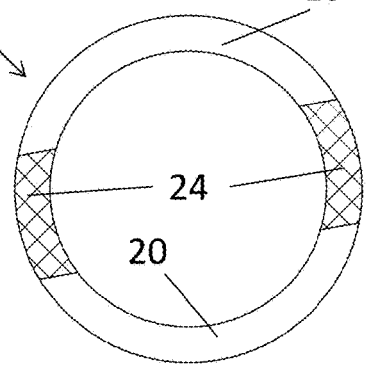
Figure 11D:
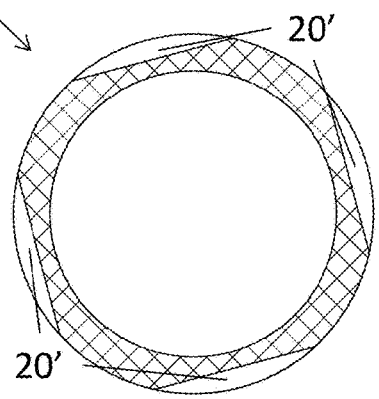
FIGS. 11D, 13D and 14C are axial cross-sectional views of the tubular member sections depicted in FIGS. 11A, 13A and 14A through respective lines labeled B-B in the corresponding side view (i.e., "A") figures.
Figure 12A:
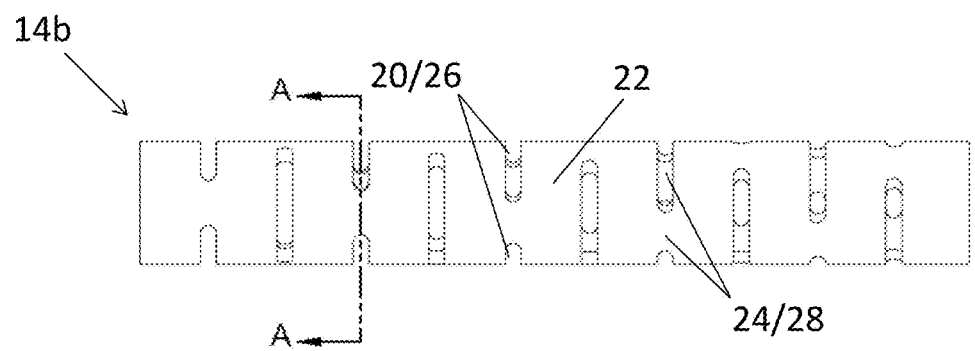
Figures 12B, 12C:
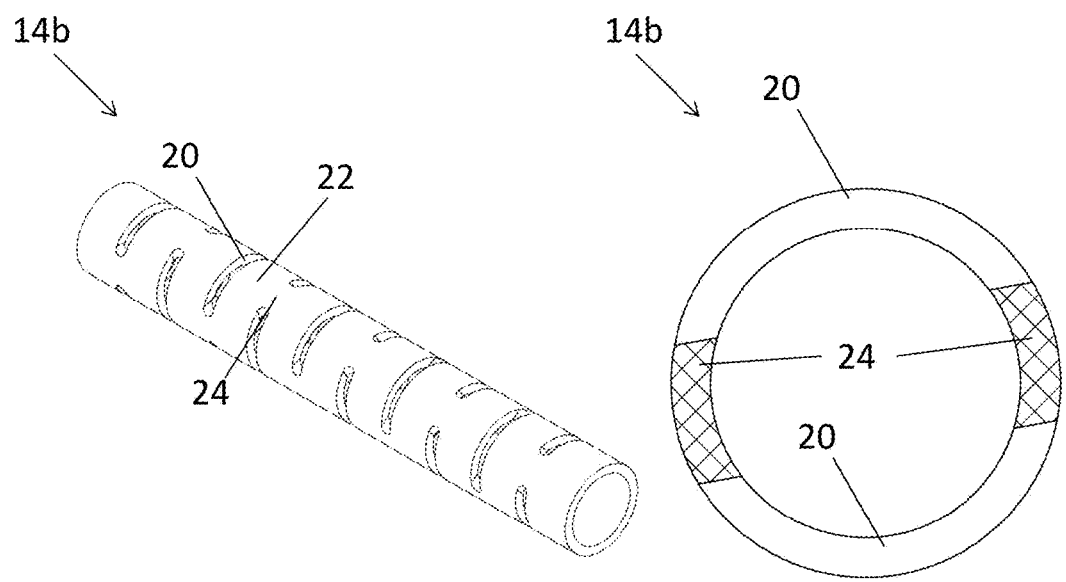

FIGS. 11A-11D and 12A-12C depict similar sections of tubular members 14 according to two embodiments. The tubular member 14 sections each include a plurality of annular segments/rings 22 connected sequentially by a corresponding plurality of groups (i.e., pairs) 28 of beams 24. The tubular member section 14a depicted in FIGS. 11A-11D is almost identical to the tubular member section 14b depicted in FIGS. 12A-12C, except that the tubular member section 14a depicted in FIGS. 11A-11D includes additional non-penetrating slots 20' disposed in the (longitudinal) middles of the rings 22. FIGS. 11A & 12A and 11B & 12B are side and perspective views, respectively. FIGS. 11C and 12C are axial cross-sectional views along respective lines labeled A-A in FIGS. 11A and 12A. FIG. 11D is an axial cross-sectional view along the line labeled B-B in FIG. 11A.

As shown in FIGS. 11C and 12C, the beams 24 of each pair 28 are disposed in the same longitudinal/axial plane, with the center of each beam 24 approximately 180 degrees displaced from the centers of the other beams 24. Each beam 24 of each pair 28 has flat walls at opposite circumferential ends of the beam 24, because the beam 24 is formed using a method (e.g., saw-cutting using blades with large diameters) that results in flat walls. The wall of the two beams 24 can be formed with two cuts.

The annular segments 22 and pairs 28 of beams 24 in FIGS. 11A-11D and 12A-12C define respective pluralities of slots 20 along the lengths of respective tubular member 14a, 14b segments. These slots 20 pass completely through the walls of respective tubular member 14a, 14b segments. Longitudinally adjacent pairs 28 of beams 24 are rotated relative to each other (about the longitudinal axis) by about 85 degrees, such that a particular beam 24 of the pair 28 appears to make a complete (360 degree) rotation about the longitudinal axis of respective tubular member 14a, 14b segments every approximately 72 pairs 28 of beams 24.

In addition, each ring 22 in the tubular member section 14a depicted in FIGS. 11A-11D includes four additional non-penetrating slots 20' disposed in the (longitudinal) middles thereof. As shown in FIG. 11D, the non-penetrating slots 20' do not penetrate the wall of the tubular member 14a. Each non-penetrating slot 20' has a flat outer surface, because the non-penetrating slot 20' is formed using a method (e.g., saw-cutting using blades with large diameters) that results in flat walls. The four non-penetrating slots 20' in each ring 22 can be formed with four cuts. Saw-cutting facilitates making non-penetrating slots.

The circumferential length of each beam 24 in FIGS. 11A-11D and 12A-12C is approximately 0.0045 in. Also, the longitudinal width of each slot 20 is approximately 0.00157 in. Further, the longitudinal spacing between each pair of adjacent slots 20 is approximately 0.00757 in. The longitudinal width of each ring 22 is equal to the longitudinal spacing of the slots minus the slot width, or 0.006 ins in this example. The resulting tubular member 14a section depicted in FIGS. 11A-11D has an EI of $4.96 \times 10^{-4}$ in$^2$/lb. The resulting tubular member 14a section depicted in FIGS. 12A-12C has an EI of $5.25 \times 10^{-4}$ in$^2$/lb. These characteristics and properties are summarized in the table in FIG. 15.

In addition, the opening volume per ring and associated slot/beam of the tubular member 14b section depicted in FIGS. 12A-12C (i.e., one set 26 of slots 20) is $3.218 \times 10^{-8}$ in$^3$. In comparison, the opening volume per ring and associated slot/beam of the tubular member 14a section depicted in FIGS. 11A-11D (i.e., one set 26 of slots 20 and one set 26' of non-penetrating slots 20') is $4.387 \times 10^{-8}$ in$^3$. Comparing the characteristics and properties of the tubular member 14a, 14b sections depicted in FIGS. 11A-11D and 12A-12C, and summarized in FIG. 15 and above, demonstrates that opening volume can be increased by about 36% while only decreasing EI by about 5.5%. Accordingly, adding non-penetrating slots to tubular member sections can significantly increase the opening volume without significantly decreasing EI. This tubular member section forming technique can be combined with others described herein to generate tubular member sections with different opening volumes and substantially similar EIs. The EI of the slotted tube with the extra non-penetrating slots (shown in FIGS. 11A-11D) can be adjusted to be equal to that of the slotted tube without the extra non-penetrating slots (shown in FIGS. 12A-12C) by a slightly increasing in the beam length in the slotted tube with the extra non-penetrating slots. This would result in a slightly reduced opening volume in the slotted tube with extra non-penetrating slots, while maintaining substantially identical EIs between the two tubes.

Changing Beam Lengths and Slot Spacing While Maintaining Opening Volume

Figure 13A:
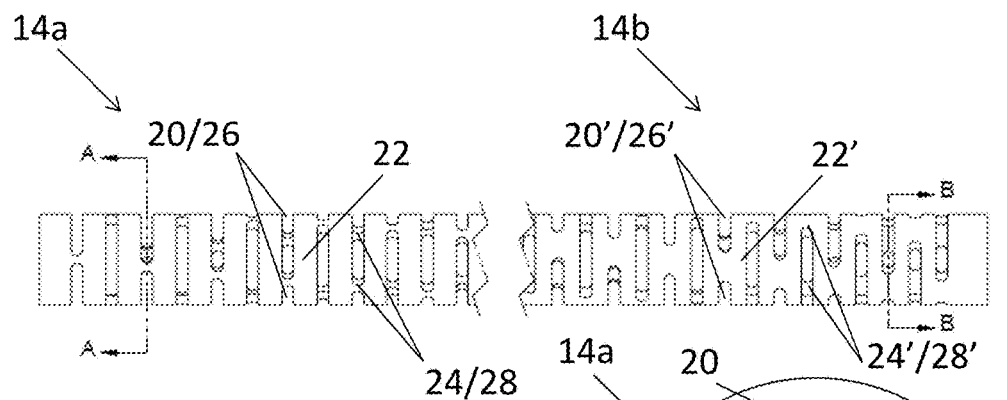
Figure 13B:
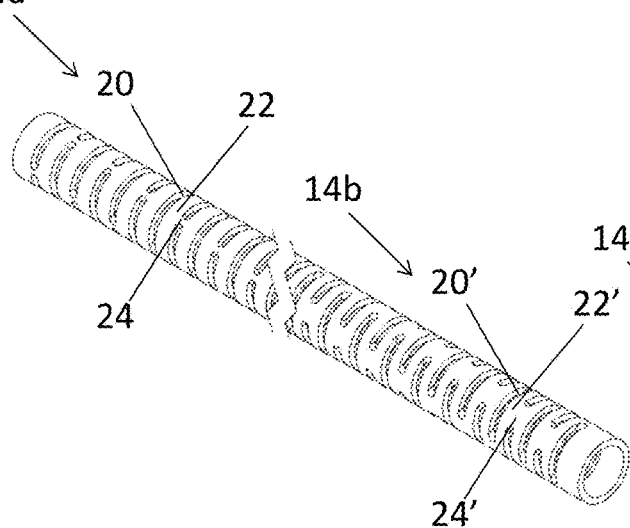
Figure 13C:
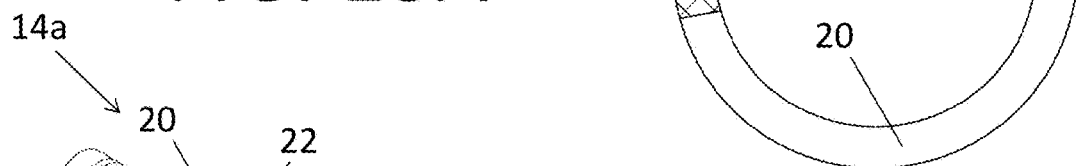
Figure 13D:
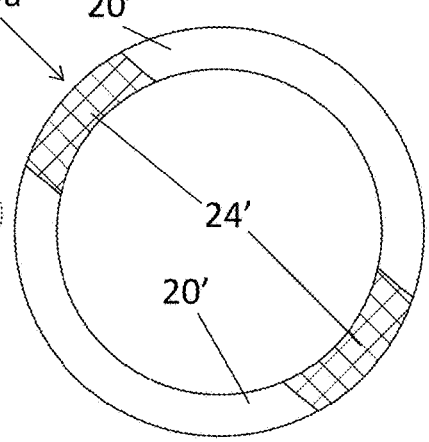

FIGS. 13A-13D depict first and second sections 14a, 14b of a tubular member according to yet another embodiment. The first and second tubular member sections 14a, 14b each include a plurality of annular first and second section segments/rings 22, 22' connected sequentially by a corresponding plurality of groups (i.e., pairs) 28, 28' of first and second section beams 24, 24'. The first tubular member section 14a is similar to the second tubular member section 14b, except that the first section beams 24 are circumferentially shorter than the second section beams 24', and the first section rings 22 are axially wider than the second section rings 22'. FIGS. 13A and 13B are side and perspective views, respectively. FIGS. 13C and 13D are axial cross-sectional views along respective lines labeled A-A and B-B.

As shown in FIGS. 13C and 13D, the first and second section beams 24, 24' of each pair 28, 28' are each disposed in the same longitudinal/axial plane, with the center of each beam 24 approximately 180 degrees displaced from the centers of the other beams 24. Each first and second section beam 24, 24' of each pair 28, 28' has flat walls at opposite circumferential ends of the beam 24, 24', because the beams 24, 24' are formed using a method (e.g., saw-laser cutting using blades with large diameters) that results in flat walls. The wall of each pair 28, 28' of two beams 24, 24' can be formed with two cuts.

The first and second section annular segments 22, 22' and pairs 28, 28' of beams 24, 24' in FIGS. 13A-13D define respective pluralities of first and second section slots 20, 20' along the lengths of respective first and second tubular member segments 14a, 14b. Longitudinally adjacent pairs 28, 28' of beams 24, 24' are rotated relative to each other (about the longitudinal axis) by about 85 degrees, such that a particular beam 24, 24' of a pair 28, 28' appears to make a complete (360 degree) rotation about the longitudinal axis of respective first and second tubular member segments 14a, 14b every approximately 72 pairs 28, 28' of beams 24, 24'.

The circumferential lengths of each first and second section beams 24, 24' are approximately $1.05 \times 10^{-3}$ in and approximately $4.81 \times 10^{-3}$ in, respectively. Also, the longitudinal widths of each first and second section slot 20, 20' are approximately 0.00157 in. Further, the longitudinal spacing between each pair of adjacent first and second section slots 20, 20' are approximately $4.73 \times 10^{-3}$ in and approximately $3.54 \times 10^{-3}$ in, respectively. The longitudinal width of each first-section ring 22 is equal to the longitudinal spacing of the slots minus the slot width, or 0.00316 ins in this example. The longitudinal width of each second-section ring 22' is equal to the longitudinal spacing of the slots minus the slot width, or 0.00197 ins in this example. The resulting first and second tubular member sections 14a, 14b have EIs of $1.60 \times 10^{-5}$ in$^2$/lb and $8.68 \times 10^{-5}$ in$^2$/lb, respectively. These characteristics and properties are summarized in the table in FIG. 15. Moreover, each of the first and second tubular member sections 14a, 14b have an opening volume of approximately $2.94 \times 10^{-5}$ in$^3$/in of tubular member. Comparing the characteristics and properties of the first and second tubular member sections 14a, 14b depicted in FIGS. 13A-13D, and summarized in FIG. 15 and above, demonstrates that tubular member sections can be formed such that they have significantly different EIs, but substantially similar opening volumes.

Changing Three Beams to Two Beams While Maintaining EI

Figure 14A:
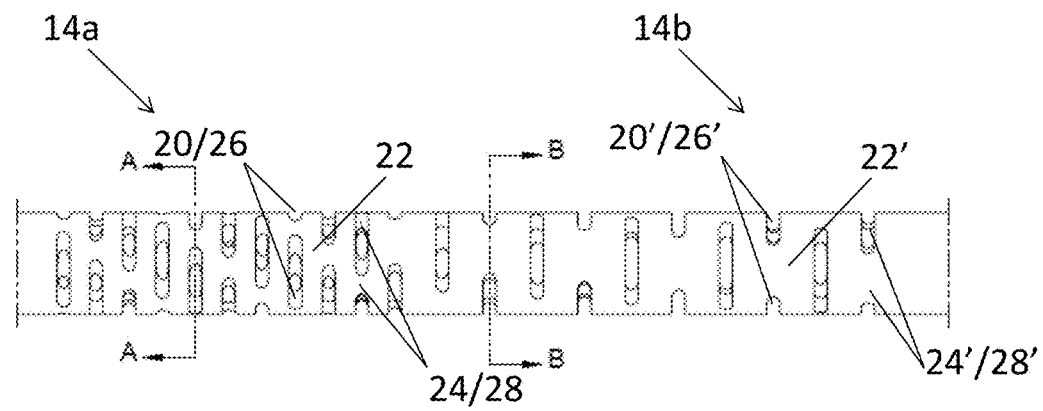
Figure 14B:
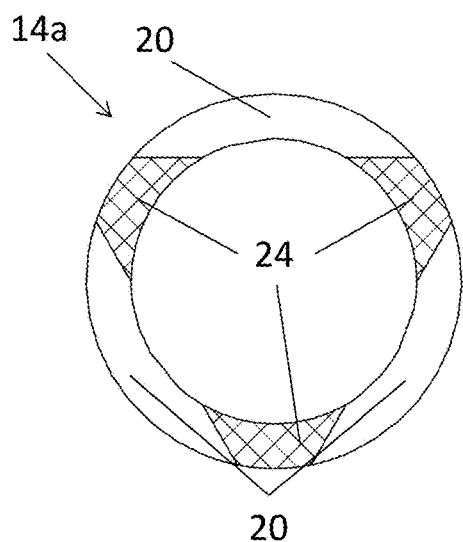
Figure 14C:
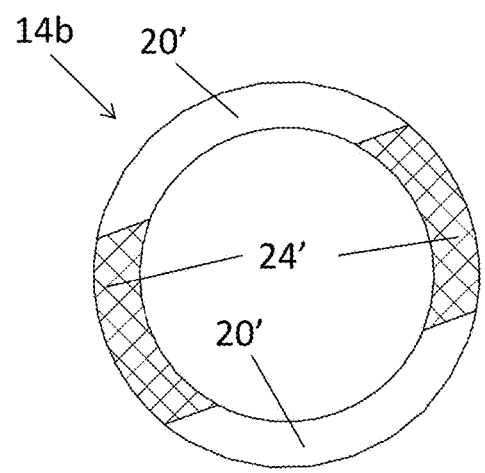

FIGS. 14A-14C depict first and second sections 14a, 14b of a tubular member according to another embodiment. The first and second tubular member sections 14a, 14b each include a plurality of annular first and second section segments/rings 22, 22' connected sequentially by a corresponding plurality of groups (i.e., triplets and pairs) 28, 28' of first and second section beams 24, 24'. The first tubular member section 14a is similar to the second tubular member section 14b, except that the first section beams 24 are grouped in triplets and circumferentially shorter than the second section beams 24', which are grouped in pairs, and the second section rings 22' are axially wider than the first section rings 22. FIG. 14A is a side view. FIGS. 14B and 14C are axial cross-sectional views along respective lines labeled A-A and B-B.

As shown in FIG. 14B, the first section beams 24 of each triplet 28 are disposed in the same longitudinal/axial plane, with the center of each beam 24 approximately 120 degrees displaced from the centers of the other beams 24. Each first section beam 24 of the triplet 28 has flat walls at opposite circumferential ends of the beam 24, because the beams 24 are formed using a method (e.g., saw-cutting using blades with large diameters) that results in flat walls. The wall of each triplet 28 of three first section beams 24 can be formed with three cuts.

As shown in FIG. 14C, the second section beams 24' of each pair 28' are disposed in the same longitudinal/axial plane, with the center of each beam 24' approximately 180 degrees displaced from the centers of the other beams 24'. Each second section beam 24' of the pair 28 has flat walls at opposite circumferential ends of the beam 24', because the beams 24' are formed using a method (e.g., saw-cutting using blades with large diameters) that results in flat walls. The wall of each pair 28' of two second section beams 24' can be formed with two cuts.

The first and second section annular segments 22, 22' and groups 28, 28' of beams 24, 24' in FIGS. 14A-14C define respective pluralities of first and second section slots 20, 20' along the lengths of respective first and second tubular member segments 14a, 14b. Longitudinally adjacent triplets 28 of first section beams 24 are rotated relative to each other (about the longitudinal axis) by about 55 degrees, such that a particular beam 24 of a triplet 28 appears to make a complete (360 degree) rotation about the longitudinal axis of the first tubular member segment 14a every approximately 72 triplets 28 of beams 24. Longitudinally adjacent pairs 28' of second section beams 24' are rotated relative to each other (about the longitudinal axis) by about 85 degrees, such that a particular beam 24' of a pair 28' makes a complete (360 degree) rotation about the longitudinal axis of the tubular member segment 14b every approximately 72 pairs 28' of beams 24'.

The circumferential lengths of each first and second section beams 24, 24' are approximately $1.55 \times 10^{-3}$ in and approximately $3.67 \times 10^{-3}$ in, respectively. Also, the longitudinal widths of each first and second section slot 20, 20' are approximately 0.00157 in. Further, the longitudinal spacing between each pair of adjacent first and second section slots 20, 20' are approximately $3.12 \times 10^{-3}$ in and approximately $5.24 \times 10^{-3}$ in, respectively. The longitudinal width of each first-section ring 22 is equal to the longitudinal spacing of the slots minus the slot width, or 0.00155 ins in this example. The longitudinal width of each second-section ring 22' is equal to the longitudinal spacing of the slots minus the slot width, or 0.00367 ins in this example. The resulting first and second tubular member sections 14a, 14b have EIs of $2.3 \times 10^{-4}$ in$^2$/lb. These characteristics and properties are summarized in the table in FIG. 15. Moreover, each of the first and second tubular member sections 14a, 14b have an opening volume of approximately $2.3 \times 10^{-6}$ in$^3$/in of tubular member and approximately $8.3 \times 10^{-6}$ in$^3$/in of tubular member, respectively. Comparing the characteristics and properties of the first and second tubular member sections 14a, 14b depicted in FIGS. 14A-14C, and summarized in FIG. 15 and above, demonstrates that tubular member sections can be formed such that they have different numbers of beams per group and opening volumes, but substantially similar EIs.

Having described various aspects of guidewires 10 and tubular members 14 sections configured to be incorporated therein according to various embodiments, methods for manufacturing fenestrated tubular members 14 will now be described.

Figure 16:
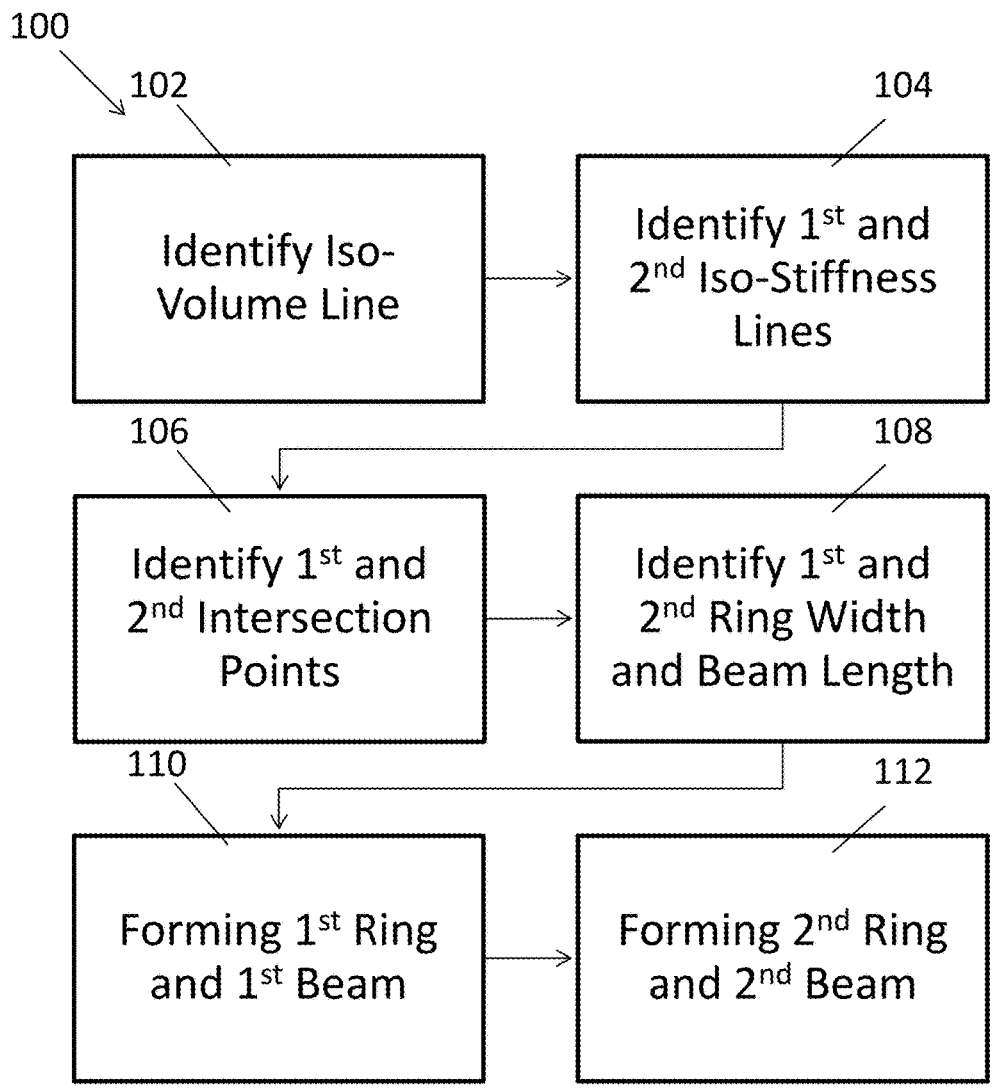
FIGS. 16, 18 and 19 are flow charts depicting methods of manufacturing fenestrated tubular members according to various embodiments.
Figure 17:
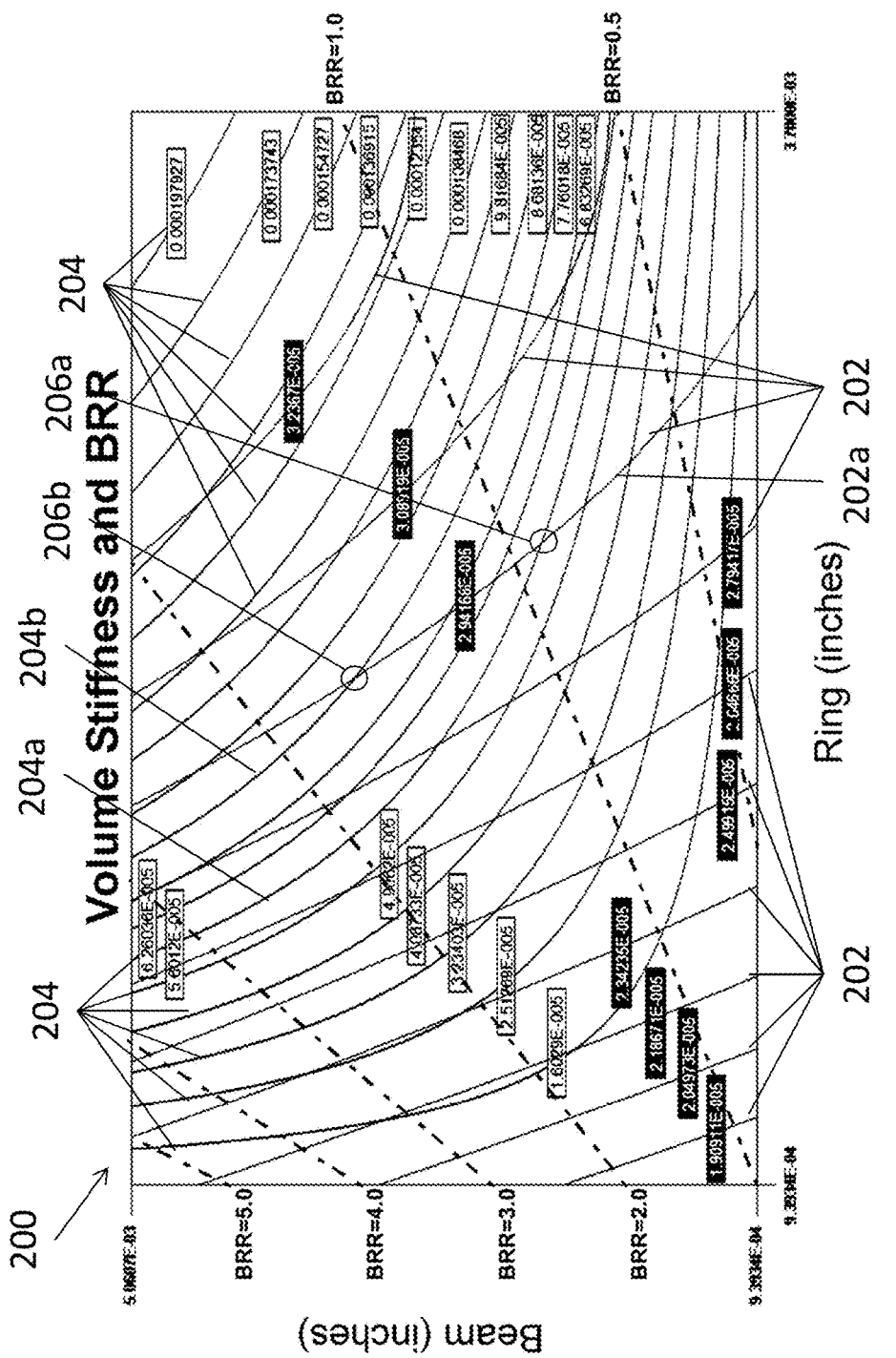
FIG. 17 is an exemplary plot for methods of manufacturing fenestrated tubular members according to various embodiments.

FIG. 16 is a flow chart depicting a method 100 of manufacturing a fenestrated tubular member 14 according to one embodiment. At step 102 an iso-volume line 202a is identified. An iso-volume line 202 is a set of tubular member characteristics that result in tubular members having a particular opening volume, as shown in FIG. 17 and described below. Tubular member characteristics include, but are not limited to, ring width, beam length, slot length, slot width, slot depth, beam centerline offset, number of slots in a cross-sectional plane, and the presence/absence/number of recesses that do not fully penetrate the wall of the tubular member. In the embodiment depicted in FIG. 16, the iso-volume line 202a is identified on a plot 200 tracking the relations between ring width and beam length of tubular members 14, as shown in FIG. 17. While the plot 200 may be a graphical display as in FIG. 17, the plot is not necessarily displayed in computer implemented embodiments. While the plot 200 in FIG. 17 tracks two tubular member characteristics (i.e., ring width and beam length), plots in other embodiments can track three or more tubular member characteristics simultaneously, resulting in analyses with three or more degrees of freedom.

In step 104, first and second iso-stiffness lines 204a, 204b are identified in the plot 200. As described above, in the embodiment depicted in FIGS. 16 and 17, the tubular member characteristics are ring width and beam length. An iso-stiffness line 204 is a set of tubular member characteristics that result in tubular members 14 having a particular stiffness. The first and second iso-stiffness lines 204a, 204b correspond to different first and second stiffnesses.

In step 106, first and second intersection points 206a, 206b are identified in the plot 200. The first and second intersection points 206a, 206b represent the ring width and beam length where the iso-volume line 202a intersects with the first and second iso-stiffness lines 204a, 204b, respectively.

In step 108, first and second ring widths and beam lengths are identified. First and second ring widths and beam lengths are the ring widths and beam lengths corresponding to the first and second intersection points 206a, 206b.

In step 110, first ring and first beam are formed in a first section 14a of the tubular member 14. The first ring has the first ring width and the first beam has the first beam length. In step 112, second ring and second beam are formed in a second section 14b of the tubular member 14. The second ring has the second ring width and the second beam has the second beam length. The first and second rings and beams can be formed in the tubular member 14 by mechanical blade cutting, laser cutting, electric discharge machining and plasma arc cutting.

Because the first and second rings and beams are formed to have the first and second ring widths and beam lengths, the first and second sections 14a, 14b of the tubular member 14 formed according the method 100 depicted in FIG. 16 will have different first and second stiffness, but substantially similar first and second opening volumes.

Figure 18:
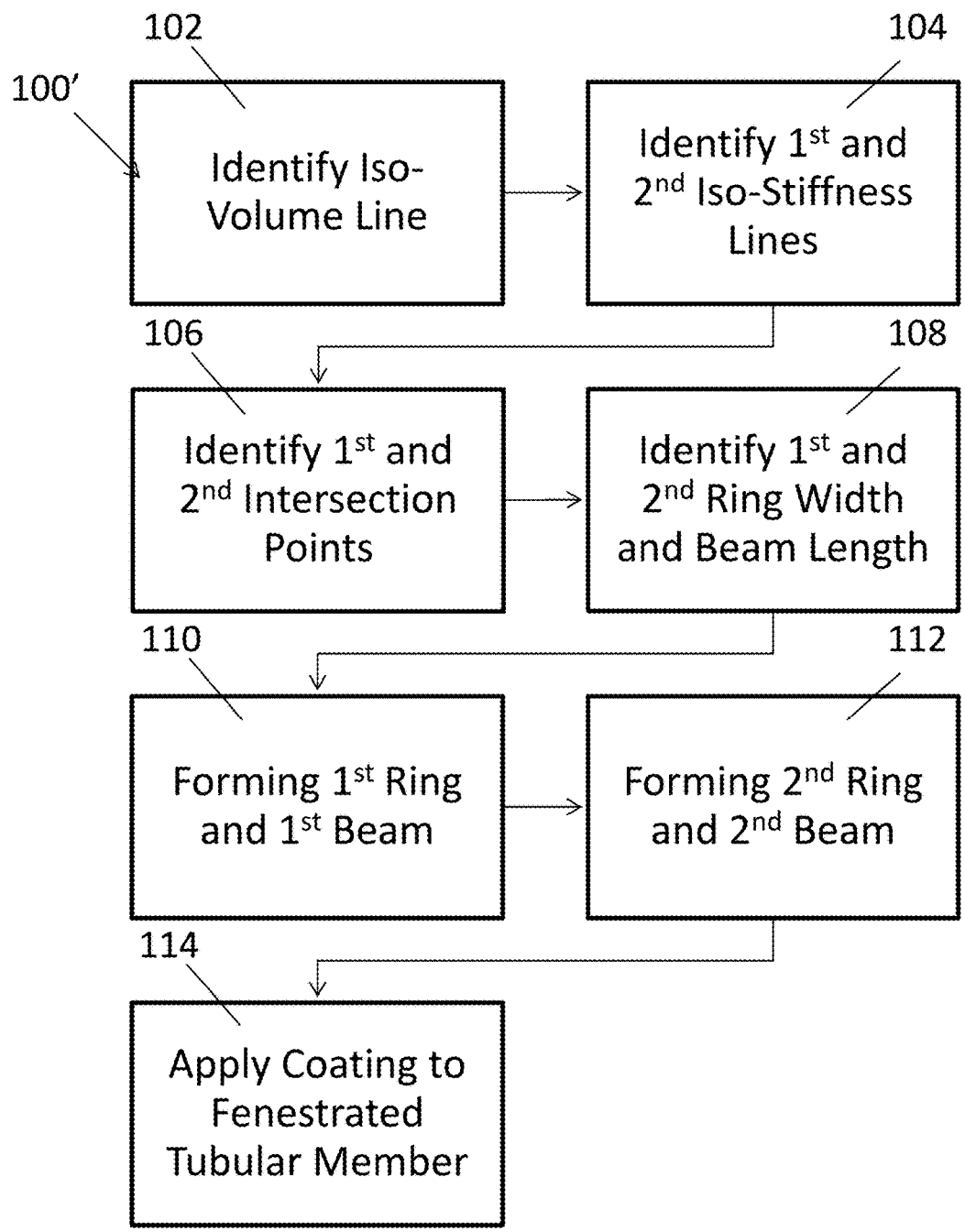

FIG. 18 is a flow chart depicting a method 100' of manufacturing a coated and fenestrated tubular member 14 according to another embodiment. Steps 102 to 112 of the method 100' depicted in FIG. 18 are identical to corresponding steps in the method 100 depicted in FIG. 16. After the first and second rings and beams are formed in steps 110 and 112, the method 100' depicted in FIG. 18 continues with the application of a coating 18 to the tubular member 14 at step 114. The coating 18 can be a polymer, such as polyurethane (e.g., a laminated TECOFLEX tube). The coating 18 can be applied using various methods, including, but not limited to, spray coating, dip coating, extrusion and lamination.

Because the first and second sections 14a, 14b of the tubular member 14 formed according the method 100' depicted in FIG. 18 have substantially similar first and second opening volumes, the first and second sections 14a, 14b of the coated tubular member will have substantially similar outer diameters. The substantially similar outer diameters is achieved in without having to vary the amount of coating 18 applied to the first and second sections 14a, 14b.

Figure 19:
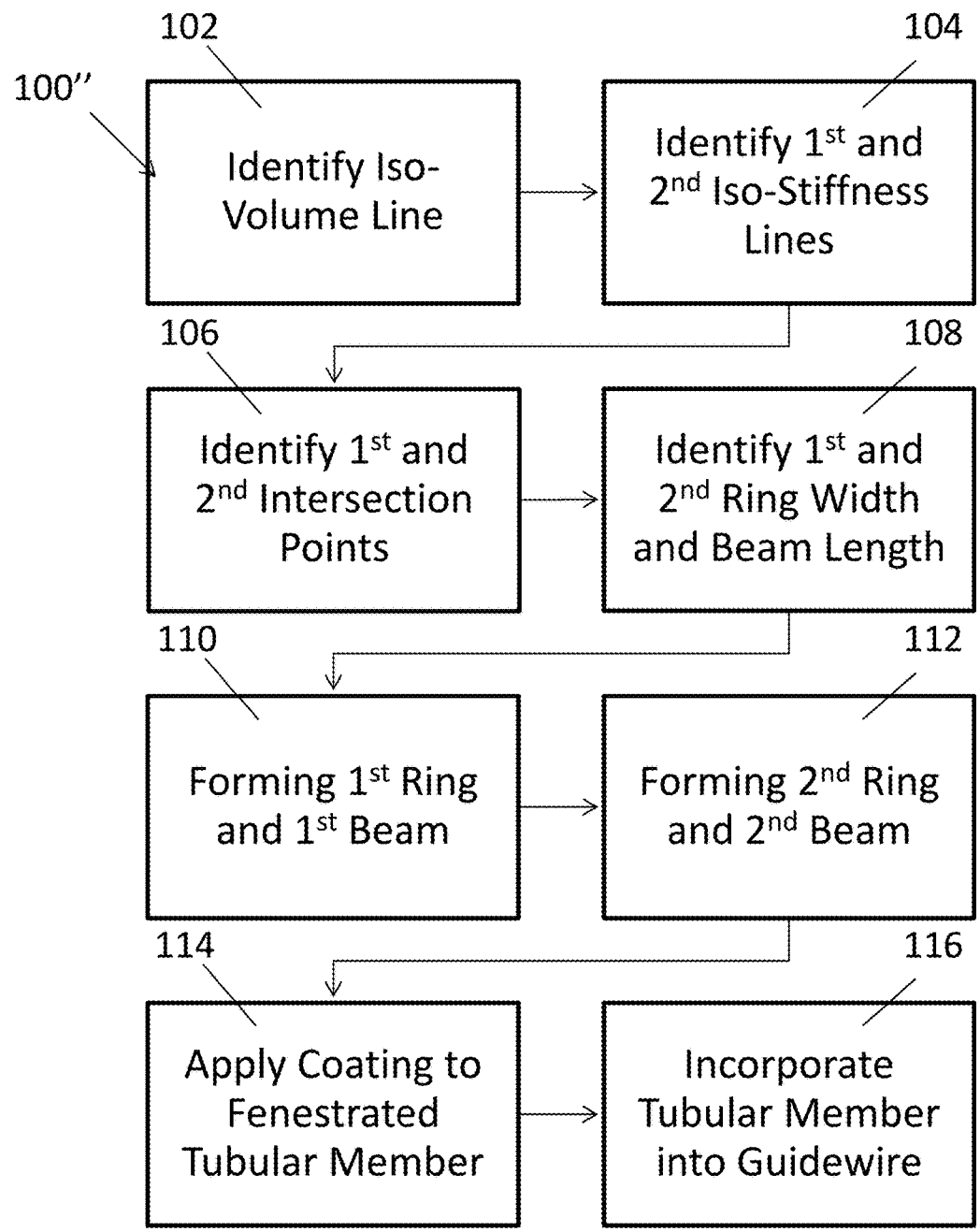

FIG. 19 is a flow chart depicting a method 100" of manufacturing a coated and fenestrated tubular member 14 according to still another embodiment. Steps 102 to 114 of the method 100" depicted in FIG. 19 are identical to corresponding steps in the method 100' depicted in FIG. 18. After the coating is applied in step 114, the method 100" depicted in FIG. 19 continues with the incorporation of the tubular member 14 into a guidewire 10. The tubular member 14 is incorporated such that the first section 14a is proximal of the second section 14b. Further, the first and second rings and beams are formed such that the first stiffness of the first section 14a is greater than the second stiffness of the second section 14b.

Because the first sections 14a of the tubular member 14 formed according the method 100" depicted in FIG. 19 is greater than the second section 14b, a proximal section of the guidewire 10 will have a higher stiffness than a distal section of the guidewire 10. However, because the first and second sections 14a, 14b of the coated tubular member have substantially similar outer diameters, so will the first and second sections of the guidewire. The substantially similar outer diameters improve the guidewire's ability to perform various functions, such as sealing a balloon catheter and insertion through tortuous vessels.

The following is a method of manufacturing fenestrated tubular members 14 according to yet another embodiment.
1. Select a raw material (e.g., Nitinol), and the outside and inside diameters of the tubing stock to be used.
2. Select a slot width.
3. Prepare a designed experiment (e.g., factorial) to create a mathematical model of slotted tube bending stiffness ("EI") and volume per unit length ("V") as functions of beam length ("BL") and ring width ("RW").
4. Generate EI data to populate the designed experiment by either creating solid models or physical specimens of slotted tubes with beam length and ring width values at each of the design points of the experiment.
   a. In the case of computer modeling, Finite Element Analysis ("FEA") can be used to determine EI.
   b. In the case of physical specimens, the EI can be directly measured.
5. Directly calculate the slotted tube volume/unit length for each of the design points.
6. Generate a plot that overlays constant-volume (iso-volume) and constant-bending-stiffness (iso-EI) contours on ring width and beam length axes.
7. Determine the range of EIs for the desired slotted tube component.
8. Choose an iso-volume contour that intersects the desired range of iso-EI contours with the most "reasonable" beam and ring values. The "reasonableness" determination can include the following factors:
   a. Avoidance of feature dimensions that are too small to be reliably manufactured with the chosen method, due to expected process variation.
   b. Avoidance of feature dimensions that are too small to be reliably manufactured, due to expected process variation in subsequent processes. For example, a feature in a laser-cut tube can be so small that subsequent etching/slag removal processes may not have sufficient control to ensure that the feature would not be completely etched away.
   c. Avoidance of feature dimensions that would not provide adequate strength to remain intact in the intended application of the slotted tube component.
   d. Avoidance of ring widths that are so large as to inhibit flow of polymer from the ring center into the slots during the lamination stage.
   e. Avoidance of beam-length-to-ring-width ratios (BL-RRs) that result in high-stress locations in bending, torsion, tension, or shear loading, or any combination of those loading conditions.
   f. Note that it may be necessary to allow the slotted tube volume/unit length to vary slightly, in order to create a slotted tube design that has "reasonable" dimensions over the full range of desired EI values.
   g. Note that it may be necessary to use a more complex mathematical model or to super-impose more than one mathematical model in order to create a slotted tube design that has "reasonable" dimensions over the full range of desired EI values.
   h. A more complex model may include variation in slot width.
   i. Super-imposition of multiple models may include, among other approaches, switching from 2-beam to 3-beam geometry, modifying slot widths, or adding slots that have minimal impact on the bending stiffness, while creating additional opening volume to contain polymer flow. Additional mathematical models can be produced (as described above) for slotted tubes with a different number of beams, or with different slot widths, and the various models employed in various sections of the slotted tube, in order to achieve the desired EI while minimizing volume variation along the length of the slotted tube.
9. Re-arrange the volume equation V=f(RW, BL) that was an output from the designed experiment to derive BL=f(V, RW).
10. Substitute this BL equation into the EI=f(RW, BL) equation from the designed experiment to derive EI as f(RW, V).
11. Rearrange this equation to derive RW=f(EI, V).
12. Enter the values of EI and V at the intersecting contours into the equation from step 11 to calculate RWs at each of these contour intersection points.
13. Enter the resultant RW values and the selected V value into the BL=f(V, RW) equation from step 9 to calculate BLs for these points.
14. Plot BL vs. EI with the above data points, then fit a curve to the data using known software, including MICROSOFT EXCEL ("TRENDLINE" function; the equation of the TRENDLINE function is BL=f (EI)).

15. Plot RW vs. BL using the above data points and fit a curve to this plot. This produces the equation RW=f (BL).

The following is a method of manufacturing fenestrated tubular members 14 according to another embodiment. This method is more graphical.

1. Choose an iso-volume contour.
2. Choose two iso-EI contours.
3. From the EI and Volume contour plots, pick the beam and ring values where the chosen iso-volume contour intersects the two iso-EI contours.
4. Plot BL vs. EI with the above data points, then fit a curve to the data using know software as described above.
5. Plot RW vs. BL using the above data points and fit a curve to this plot. This produces the equation RW=f (BL).
6. Note that it is also possible to choose one parameter (BL or RW) from the contour intersections, then re-arrange the EI=f(RW, BL) or V=f(RW, BL) equation to calculate the other parameter, using the V and EI values at each contour intersection point.

The following is a method of creating the slotted tube design after the slotted tube characteristics are determined.

1. From the desired performance characteristics, determine the desired EI=f(x) for the slotted tube, as describes above, where x is position along the length of the slotted tube.
2. Use EI=f(x) and BL=f(EI) to calculate the function BL=f(x).
3. Use BL=f(x) and RW=f(BL) to calculate the function RW=f(x)
4. The above equations fully define the design of the slotted tube, given fixed tube stock dimensions and slot width.

While the embodiments herein describe manufacturing coated fenestrated tubes having a pre-determined outer diameter, components inside of a fenestrated tube (e.g., core-wires, coils, etc.) may affect the outer diameter after lamination. Accordingly, the opening/fenestration volume of the fenestrated tube can be manipulated according to the methods described herein, to accommodate the outer diameter change caused by the components inside of the fenestrated tube. While the embodiments herein describe manufacturing coated fenestrated tubes having a pre-determined outer diameter, the methods described herein can be applied equally to coated wires having slots formed on the outer surface thereof. While the embodiments herein describe beam configurations that are symmetrical about at least one axis, the invention is not so limited. For instance, a coated fenestrated tube (or a portion thereof) may have two or more beams are of different lengths, with or without a beam centerline offset.

While the embodiments herein describe varying specific fenestrated tube characteristics to achieve specific opening volumes and EIs, many different approaches can achieve the same desired results. For instance, fenestrated tube characteristics other than beam length and ring width can be used in the mathematical models. Also, different parameters can be used to create the final fenestrated tube design (e.g., torsional stiffness rather than bending stiffness, etc.)

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in anillustrative rather than restrictive sense.

What is claimed is:

1. A method of forming a fenestrated tubular support member, the formed fenestrated tubular support member comprising a first section having a first pattern of successive first section annular rings connected by respective first section axial beams, and a second section having a second pattern of successive second section annular rings connected by respective second section axial beams, wherein each of the first section annular rings has a first section ring width and each of the first section beams has a first section beam length, wherein each of the second section annular rings has a second section ring width and each of the second section beams has a second section beam length, and wherein the first section has a first stiffness and the second section has a second stiffness different than the first stiffness, the method of forming the fenestrated tubular support member comprising:

determining a first iso-stiffness curve corresponding to a first function of beam length versus ring width for the first stiffness;

determining a second iso-stiffness curve corresponding to a second function of beam length versus ring width for the second stiffness;

determining an iso-volume curve corresponding to a third function of beam length versus ring width for a given fenestration volume;

identifying a first intersection point where the iso-volume curve intersects the first iso-stiffness curve; and identifying a second intersection point where the iso-volume curve intersects the second iso-stiffness curve, wherein the first section ring width and first section beam length are determined from the first intersection point, and the second section ring width and second section beam length are determined from the second intersection point, forming the first pattern into a first section of a tube such that the first section has the first stiffness; and forming the second pattern into a second section of the tube such that the second section has the second stiffness.

2. The method of claim 1, wherein forming the first and second patterns comprises processing the respective first and second sections of the tube using a technique selected from the group consisting of micro-machining, laser-cutting, saw-cutting, electron discharge machining, grinding, milling, casting, molding, chemically etching, 3D printing, and other additive methods.

3. The method of claim 1, further comprising applying a coating material to the first and second sections of the tube to form respective first and second coated sections of the tube.

4. The method of claim 3, wherein applying the coating material comprises treating the respective first and second sections of the tube using a technique selected from the group consisting of spraying coating, dip coating, extrusion and lamination.

5. The method of claim 3, wherein forming the first and second patterns comprises forming first fenestrations in the first section of the tube, and forming second fenestrations in the second section of the tube.

6. The method of claim 5, wherein the applying the coating material comprises substantially filling the first and second fenestrations with the coating material.

7. The method of claim 3, wherein the coated first section has a first outer diameter, and the coated second section has a second outer diameter substantially the same as the first outer diameter.

8. A method of forming a fenestrated tubular support member, the formed fenestrated tubular support member comprising a first section having a first pattern of successive annular rings connected by respective axial beams, and a second section having a second pattern of successive annular rings connected by respective axial beams, wherein each of the first section annular rings has a first section ring width and each of the first section beams has a first section beam length, wherein each of the second section annular rings has a second section ring width and each of the second section beams has a second section beam length, wherein the first section has a first stiffness and the second section has a second stiffness different than the first stiffness, and wherein the first section has a first fenestration volume, and the second section has a second fenestration volume different than the first fenestration volume, the method of forming the fenestrated tubular support member comprising:

determining a first iso-stiffness curve corresponding to a first function of beam length versus ring width for the first stiffness;

determining a second iso-stiffness curve corresponding to a second function of beam length versus ring width for the second stiffness;

determining a first iso-volume curve corresponding to a third function of beam length versus ring width for the first fenestration volume;

determining a second iso-volume curve corresponding to a fourth function of beam length versus ring width for the second fenestration volume;

identifying a first intersection point where the first iso-volume curve intersects the first iso-stiffness curve; and identifying a second intersection point where the second iso-volume curve intersects the second iso-stiffness curve, wherein the first section ring width and first section beam length are determined from the first intersection point, and the second section ring width and second section beam length are determined from the second intersection point forming the first pattern into a first section of a tube such that the first section has the first stiffness; and forming the second pattern into a second section of the tube such that the second section has the second stiffness.

9. The method of claim 8, wherein forming the first and second patterns comprises processing the respective first and second sections of the tube using a technique selected from the group consisting of micro-machining, laser-cutting, saw-cutting, electron discharge machining, grinding, milling, casting, molding, chemically etching, 3D printing, and other additive methods.

10. The method of claim 8, further comprising applying a coating material to the first and second sections of the tube to form respective first and second coated sections of the tube.

11. The method of claim 10, wherein applying the coating material comprises treating the respective first and second sections of the tube using a technique selected from the group consisting of spray coating, dip coating, extrusion and lamination.

12. The method of claim 10, wherein forming the first and second patterns comprises forming first fenestrations in the first section of the tube, and forming second fenestrations in the second section of the tube.

13. The method of claim 12, wherein the applying the coating material comprises substantially filling the first and second fenestrations with the coating material.

14. The method of claim 10, wherein the coated first section has a first outer diameter, and the coated second section has a second outer diameter different from first outer diameter.

* * * * *